(12) United States Patent
Gretz et al.

(10) Patent No.: US 9,632,094 B2
(45) Date of Patent: Apr. 25, 2017

(54) TRANSCUTANEOUS ORGAN FUNCTION MEASUREMENT

(75) Inventors: Norbert Gretz, Mannheim (DE); Johannes Pill, Leimen (DE); Daniel Schock-Kusch, Mannheim (DE); Thomas Walter, Mühlhausen (DE); Jürgen Hesser, Heidelberg (DE); Maliha Sadick, Hassloch (DE); Felix Eickemeyer, Heidelberg (DE); Jae Hyung Hwang, Viernheim (DE); Christian Schildknecht, Mannheim (DE); Soichi Watanabe, Mannheim (DE); Wolfgang Wach, Worms (DE); Thomas Rose, Worms (DE)

(73) Assignee: Norbert Gretz, Mannheim (DE)

( * ) Notice: Subject to any disclaimer, the term of this patent is extended or adjusted under 35 U.S.C. 154(b) by 1055 days.

(21) Appl. No.: 13/060,260

(22) PCT Filed: Aug. 20, 2009

(86) PCT No.: PCT/EP2009/060785
§ 371 (c)(1),
(2), (4) Date: May 27, 2011

(87) PCT Pub. No.: WO2010/020673
PCT Pub. Date: Feb. 25, 2010

(65) Prior Publication Data
US 2011/0230739 A1    Sep. 22, 2011

(30) Foreign Application Priority Data
Aug. 22, 2008   (EP) .................................. 08162802

(51) Int. Cl.
*A61B 5/00*   (2006.01)
*G01N 33/58*   (2006.01)
(Continued)

(52) U.S. Cl.
CPC ........... *G01N 33/582* (2013.01); *A61B 5/145* (2013.01); *A61B 5/1455* (2013.01);
(Continued)

(58) Field of Classification Search
CPC ... A61B 5/1455; A61B 5/6833; A61B 5/0002; A61B 5/145; A61B 5/14546;
(Continued)

(56) References Cited

U.S. PATENT DOCUMENTS 5,403,928 A * 4/1995 Arrhenuis .................... 540/128
6,689,616 B1   2/2004 Bosies et al.
(Continued)

FOREIGN PATENT DOCUMENTS

DE         100 23 051 A1   11/2001
DE   10 2004 048 864 A1    4/2006
(Continued)

OTHER PUBLICATIONS

Pais et al., "High-Sensitivity, disposable lab-on-a-chip with thin-film organic electronics for fluorescence detection," *The Royal Society of Chemisry*, pp. 794-800 (2008).
(Continued)

*Primary Examiner* — Elmer Chao
(74) *Attorney, Agent, or Firm* — Armstrong Teasdale LLP

(57) ABSTRACT

A sensor plaster (116) for the transcutaneous measurement of an organ function, more particularly of a kidney function, is proposed. The sensor plaster (116) comprises at least one flexible carrier element (134) having at least one adhesive surface (138) which can be stuck onto a body surface. Furthermore, the sensor plaster (116) comprises at least one radiation source, more particularly a light source (142), wherein the radiation source is designed to irradiate the body surface with at least one interrogation light (162). Furthermore, the sensor plaster (116) comprises at least one detector
(Continued)

(146) designed to detect at least one response light (176) incident from the direction of the body surface.

15 Claims, 6 Drawing Sheets

(51) Int. Cl.
*A61B 5/145* (2006.01)
*A61B 5/1455* (2006.01)
*A61B 5/20* (2006.01)
*A61K 49/00* (2006.01)

(52) U.S. Cl.
CPC .......... *A61B 5/14546* (2013.01); *A61B 5/201* (2013.01); *A61B 5/6833* (2013.01); *A61K 49/0043* (2013.01); *A61B 5/0002* (2013.01); *A61B 2560/0219* (2013.01); *A61B 2560/0412* (2013.01); *G01N 2800/065* (2013.01); *G01N 2800/28* (2013.01); *G01N 2800/347* (2013.01)

(58) Field of Classification Search
CPC ................ A61B 5/201; A61B 1/0684; A61B 2560/0219; A61B 2560/0412; A61K 49/0043; G01N 33/582; G01N 2800/065; G01N 2800/28; G01N 2800/347
See application file for complete search history.

(56) References Cited

U.S. PATENT DOCUMENTS

| | | | |
|---|---|---|---|
| 6,720,572 B1* | 4/2004 | Jackson et al. | 257/40 |
| 6,995,019 B2 | 2/2006 | Hein et al. | |
| 2004/0022730 A1* | 2/2004 | Hein et al. | 424/9.6 |
| 2004/0065806 A1* | 4/2004 | Bradley et al. | 250/214.1 |
| 2004/0197267 A1* | 10/2004 | Black et al. | 424/9.6 |
| 2004/0210280 A1 | 10/2004 | Liedtke | |
| 2005/0137459 A1* | 6/2005 | Chin et al. | 600/179 |
| 2006/0020216 A1 | 1/2006 | Oishi et al. | |
| 2007/0038046 A1* | 2/2007 | Hayter | 600/317 |
| 2007/0218563 A1 | 9/2007 | Pill et al. | |
| 2007/0237678 A1 | 10/2007 | Roesicke et al. | |
| 2008/0082004 A1 | 4/2008 | Banet et al. | |

FOREIGN PATENT DOCUMENTS

| | | |
|---|---|---|
| EP | 1 707 114 A1 | 10/2006 |
| EP | 1 752 085 A2 | 2/2007 |
| WO | WO 99/31183 | 6/1999 |
| WO | WO 01/85799 A1 | 11/2001 |
| WO | WO 2006/032441 A2 | 3/2006 |

OTHER PUBLICATIONS

Qi et al., "Serial determination of glomerular filtration rate in consciences mice using FITC-inulin clearance," *Am. J. Physiol Renal Physiol*, vol. 286, pp. F590-F596 (2004).
Anonym: Biohemicals & Reagents for Life Science Research, 2004-2005, 2004, Sigma-Aldrich Co., Ltd., p. 1115.
Samuel, "Light fantastic," *Materials World*, pp. 28-30:(2007).
Pill et al., "Direct fluorometric analysis of a newly synthesized fluorescein-labelled marker for glomerular filtration rate," *Anal. Bioanal. Chem.*, vol. 382, pp. 59-64 (2005).
Pill et al., "Fluorescein-labeled sinistrin as marker of glomerular filtration rate," *European Journ. of Medicinal Chemistry*, vol. 40, pp. 1056-1061 (2005).
Scholze et al., "Fluorescent Inhibitors for the Qualitative and Quantitative Analysis of Lipolytic Enzymes," *Analytical Biochemistry*, vol. 276, pp. 72-80 (1999).
Negre-Salvayre et al., "Hydrolysis of Fluorescent Pyrene-Acyl Esters by Human Pancreatic Carboxylic Ester Hydrolase and Bile Salt-Stimulated Lipase," *LIPIDS*, vol. 25, No. 8, pp. 428-434 (1990).
International Preliminary Report on Patentability in related International Patent Application No. PCT/EP2009/060785, dated Feb. 22, 2011.

* cited by examiner

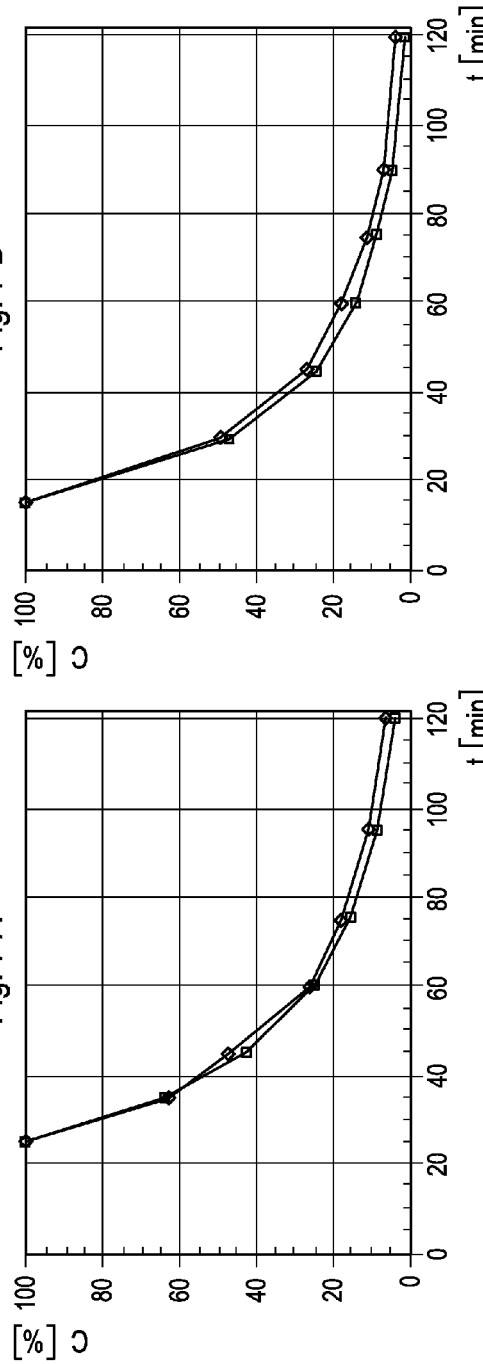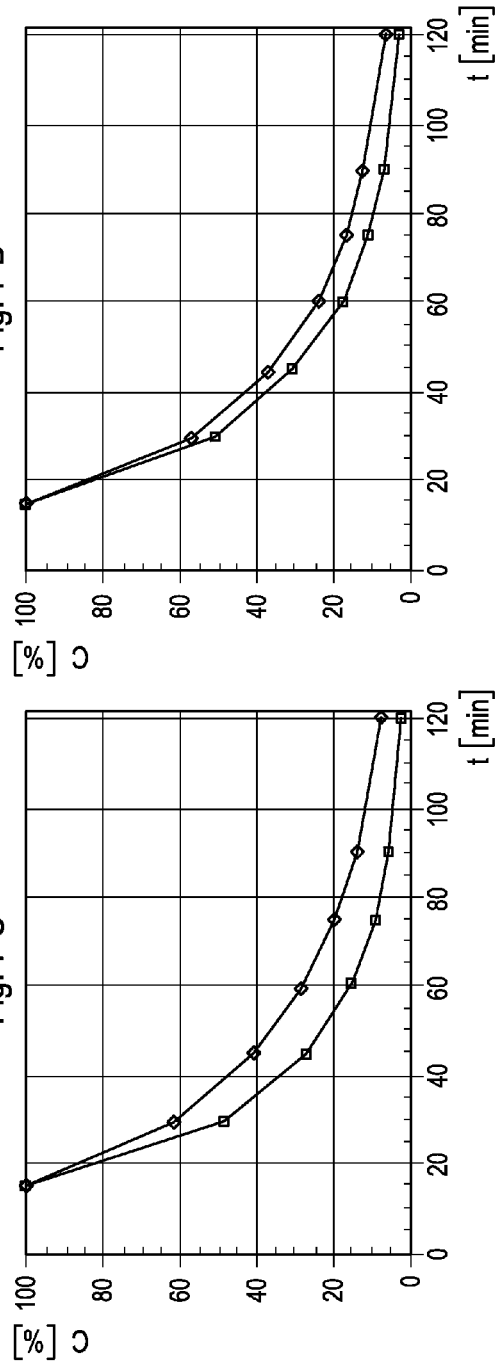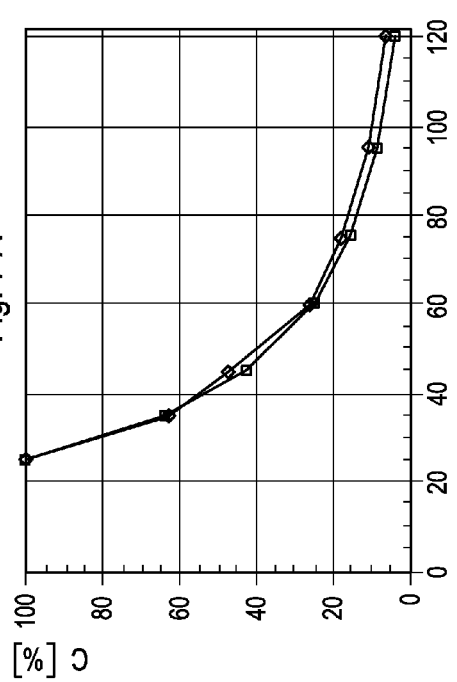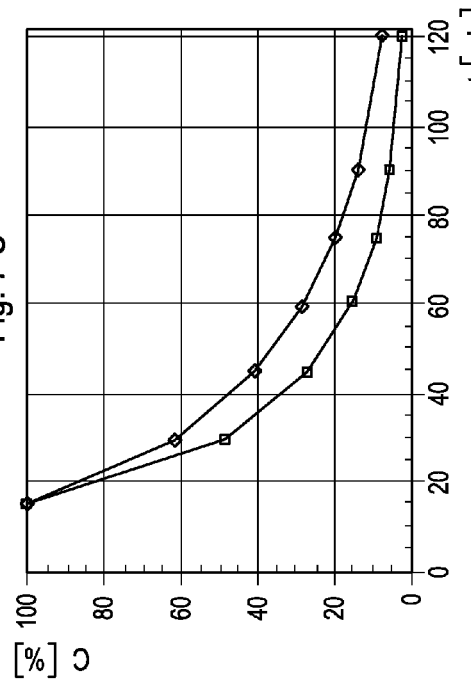

TRANSCUTANEOUS ORGAN FUNCTION MEASUREMENT

The invention relates to sensor plasters, sensor systems, kits, and the uses thereof, and a method for producing a sensor plaster, a method for the transcutaneous measurement of an organ function and a use of a fluorescence-marked indicator substance for producing a diagnostic aid. Such devices and methods can be used more particularly for measuring a kidney function, more particularly for measuring a glomerular filtration rate. However, other applications are also conceivable, in principle.

In the clinical and preclinical field, determining various organ functions is accorded great importance since, for example, corresponding therapies or medications can be controlled in accordance with said organ functions. The invention is described hereinafter substantially with regard to the kidney function. In principle, however, other applications are also conceivable in which the function of a particular organ can be detected by means of determining a temporal profile of an indicator substance.

In kidney diagnostics, the quantitative and qualitative functional testing of the kidneys is of great significance. One indicator of the kidney function is the so-called glomerular filtration rate (GFR). This should be understood to mean indirectly the amount of primary urine produced by the glomeruli of the kidneys per unit time.

For quantifying the glomerular filtration rate, several methods are known from the prior art and medical practice. One class of methods, into which the present invention is also to be classified, is based on the use of one or a plurality of indicator substances. Thus, in principle, it is possible to use any desired exogenous or endogenous substances in the blood as indicator substances which are at least predominantly removed from the blood on account of the kidney function. This means that the indicator substance is removed from the body at least predominantly by the filtration effect of the glomeruli, in which case substantially neither tubular secretion nor resorption from the primary urine takes place. The removal of the indicator substance from the blood is also referred to as renal clearance. In this case, clearance is generally designated as that amount of plasma in milliliters which is freed of the indicator substance by the kidneys per minute.

Various exogenous and/or endogenous indicator substances are known for determining the renal clearance and hence the glomerular filtration rate. Examples of endogenous indicator substances are creatinine or cystatin C. Various exogenous indicator substances are also known from the prior art. More particularly, saccharides, e.g. polyfructosans, can be used as indicator substances. Examples of suitable indicator substances are disclosed in WO2001/85799 or WO2006/32441. It is generally possible to have recourse to this prior art in the context of the present invention as well.

From a metrological standpoint, one of the challenges consists, in particular, in determining the concentration profile of the indicator substance and thus the clearance thereof. Numerous different methods by means of which the clearance can be detected metrologically are compiled in WO 99/31183. Thus, some of the methods are based on the fact that blood and/or urine samples are taken at regular or irregular intervals, and the concentration of the marker substance is determined analytically, for example by means of enzymatic detection methods. Other methods are based on the use of radioactive indicator substances and/or X-ray contrast media. The acceptance of such indicator substances by the patient is generally low, however. Methods based on determining the renal clearance by means of chemical or biochemical analysis or on the use of radioactive indicator substances are generally complex and burdened with high errors. In routine clinical practice, therefore, in many cases the kidney function is estimated on the basis of approximation formulae, which, however, are likewise very inaccurate and can have error tolerances in the range of 30 to 40%.

The prior art therefore likewise discloses methods based on the use of fluorescent markers. In this case, use is made of indicator substances marked with dyes that can be detected optically. By way of example, these can be fluorescent markers which are admixed with the indicator substances or bonded to the indicator substances, for example by covalent bonding. Examples of marked indicator substances are described in WO2001/85799 or WO2006/32441, in which case it is possible to have recourse to these marked indicator substances, for example, in the context of the present invention.

In the latter methods mentioned, therefore, an optical signal is used as a measure of the concentration of the indicator substance. In this case, the respective concentration of the indicator substance can be deduced for example from a known relation between the optical signal and the concentration. Said known relation can be, for example, of an empirical, semi-empirical or analytical nature, for example a relation determined by means of calibration measurements. Thus, in DE 100 23 051 A1, for example, the indicator substance used is sinistrin marked with fluoresceinisothiocyanate (FITC). In this case, a noninvasive, transcutaneous measurement of the FITC fluorescence signal by means of a noninvasive measuring head is described, inter alia. Said measuring head is configured as a fiber-optic measuring head in which an external light source, via an optical fiber, illuminates the skin and excites the FITC-sinistrin molecules contained therein. The fluorescent light emitted by the FITC is in turn picked up by means of optical fibers and forwarded to an external detector.

However, the measurement of the fluorescence signals as described in DE 100 23 051 A1 is extremely complex in terms of apparatus technology. This is because it is necessary to provide complex spectrographs in order to evaluate the measurement signals. Moreover, a fiber-optic system is required which, on account of the associated losses of excitation light, necessitates the use of highly intensive light sources, more particularly lasers. The fiber-optic system, together with the complex light sources and lasers, has the effect, however, that a measurement of the renal clearance cannot be carried out in an ambulant manner or by means of portable equipment, but rather practically exclusively in optical laboratories specifically designed for this purpose.

Numerous further analysis systems which, in principle, are also suitable for portable equipment are generally known from other fields of medical diagnostics. Thus, US 2004/0210280 A1, for example, describes a plaster-like system which can be used for transdermal therapy and diagnosis. Said document proposes, inter alia, that the system independently collects and takes up fluid samples from the skin.

In A. Pais et al.: High-sensitivity, disposable lab-on-a-chip with thin-film organic electronics for fluorescence detection, Lab Chip, 2008, 8, 794-800, a disposable lab-on-a-chip test element is proposed. The latter is based on an organic light-emitting diode and an organic photodetector. The test element is configured as a microfluidic test element and is able to analyze liquid samples by means of fluorescence detection.

DE 10 2004 048 864 A1 describes an analytical test element with wireless data transmission which is used for determining the concentration of an analyte from a body fluid. Said document proposes configuring at least a portion of the electrical components of the system on the basis of polymer electronics.

US 2006/020216 A1 describes a portable health management apparatus that can be used, in particular, for a blood pressure measurement. Said document proposes, inter alia, measuring the movement of the blood within a blood vessel by means of light absorption of light incident transdermally.

Methods and devices in which a skin surface is irradiated with light from a light source are likewise known from the field of medical therapeutics. Thus, a device for the photodynamic therapy of skin cancer diseases is described, for example, in I. Samuel: "Light fantastic", Materials World, August 2007, 28-30. This prior art proposes, inter alia, using a self-adhesive plaster with an organic light-emitting diode in order to irradiate the cream arranged between the plaster and the skin surface. The surrounding cancer tissue is then destroyed by the photochemical reaction.

Generally, for kidney function testing in the prior art, recourse is regularly had to inulin as the gold standard. In this case, the inulin measurement is usually effected enzymatically, i.e. in a serum or urine sample taken. Noninvasive methods using fluorescence-marked inulin yielded ambiguous results (WO2001/85799). FITC sinistrin was established as the standard for fluorescence-based GFR determinations (WO2001/85799; Pill 2005, Anal Bioanal Chem 382: 59-64; Pill 2005, Europ J Medicinal Chem 40: 1056-1061), wherein here as well the measurements were predominantly effected in isolated samples.

However, these last-mentioned methods and devices known from the prior art are generally comparatively complex in respect of apparatus. Thus, systems based on sample collection, such as, for example, the system described in the publication by A. Pais et al., generally require a technically complex microfluidic system, which can generally only be realized by means of corresponding microchannel structures. The other systems described are also generally technically comparatively complex. Moreover, none of the systems described can be employed directly for a measurement of a kidney function.

Consequently, one object of the present invention is to provide devices and methods for determining organ functions, more particularly a kidney function, which avoid the disadvantages of known devices and methods. More particularly, the intention is to provide a device which is simple to handle and which also allows a simple, fast and nevertheless reliable measurement of the organ function without considerable interruption of the daily routine of the patients or at least in the context of an ambulant treatment. This object is achieved by means of the invention with the features of the independent claims. Advantageous developments of the invention, which can be realized individually or in combination, are presented in the dependent claims.

In this case, a sensor plaster, a sensor system comprising the sensor plaster, a kit comprising the sensor plaster or the sensor system, uses of the sensor plaster, of the sensor system or of the kit, and a method for producing the sensor plaster, methods for the transcutaneous measurement of an organ function are proposed and uses of a fluorescence-marked indicator substance for producing a diagnostic aid are proposed, which can optionally also be combined. Thus, by way of example, the method for the transcutaneous measurement of an organ function can be carried out using one or more of the proposed devices, such that, for possible optional configurations of the method, reference may be made to the description of the respective devices. Conversely, the devices can be designed to carry out a corresponding method. Thus, by way of example, in the devices, for example the sensor plaster, the sensor system or the kit, it is possible to provide one or a plurality of data processing units designed in respect of programming, for example, to perform partial steps of the predefined method in one of the embodiments described below.

One basic concept of the present invention consists in improving known optical devices and methods for determining the organ function, for example the kidney function, by using small, integrated sensor plasters. Thus, a first aspect of the invention proposes a sensor plaster for the transcutaneous measurement of an organ function, more particularly of a kidney function, which can be used for example for the measurement of the renal clearance in accordance with the above description of the prior art. In this case, in the context of the present invention, a plaster is generally understood to mean a medical article comprising at least one flexible carrier element having at least one adhesive surface which can be applied, more particularly stuck, onto a body surface. Said flexible carrier element can comprise for example a plastic, a textile, a ceramic, a paper or a combination of the aforementioned and/or other materials. The sensor plaster can therefore be configured in self-adhesive fashion and can comprise one or a plurality of adhesives on the adhesive surface, for example. In a storage stage, the adhesives can be protected by one or a plurality of protective films, for example, which can be pulled off, for example. This adhesive surface can therefore enable a cohesive connection between the sensor plaster and the body surface. In principle, however, alternatively or additionally, other types of connections between the adhesive surface and the body surface are also possible, for example force-locking connections. Thus, by way of example, the adhesive surface can be pressed onto the body surface by means of one or a plurality of clamping devices, for example by means of a finger clamp or some other type of mechanical device which can provide a press-on force for pressing the adhesive surface onto the body surface. However, the use of self-adhesive adhesive surfaces is particularly preferred. In principle, therefore, the adhesive surface can be configured as a self-adhesive adhesive surface. Alternatively or additionally, however, in principle, adhesive surfaces are also conceivable in which one or a plurality of adhesives can subsequently be applied in order to enable the connection. By way of example, by means of an adhesive tube, skin-compatible adhesives can be applied to the adhesive surface in order then to stick the sensor plaster onto the body surface.

In this case, in principle, any desired surfaces of a body of a human or animal patient come into consideration as a body surface. Examples that may be mentioned include skin surfaces, surfaces of fingernails or toenails or other surfaces, more particularly surfaces exposed to the atmosphere. Generally, in this case, in the context of the present invention, the term "patient" is used for a human or an animal on whom or which one or a plurality of the proposed devices and/or methods are intended to be used, independently of whether said human or said animal is healthy or ill.

Furthermore, the sensor plaster comprises at least one radiation source. In this case, a radiation source is understood to be any device which can emit radiation. This can be, more particularly, electromagnetic radiation, for example light in the visible and/or infrared and/or ultraviolet spectral range and/or gamma radiation. Alternatively or additionally, however, in principle, other types of radiation can also be used, for example streams of particles. By way of example alpha rays and/or beta rays can be mentioned in this connection. The radiation source is correspondingly configured for generating radiation of the type mentioned. Without restricting the possible further configurations of the radiation, hereinafter the radiation is generally designated as "light", the handling of the radiation as "optical system", and the radiation source is described more particularly with reference to a light source. However, other configurations of the radiation source are also possible, in principle, and it is also possible, for example, to combine different types of radiation sources.

The radiation source can be, in particular, an integral constituent of the plaster, for example in the context of a layer construction of the sensor plaster. The radiation source is therefore designed to generate at least one interrogation light directly within the sensor plaster, in contrast to external generation of the interrogation light. In this respect, the sensor plaster differs for example from the fiber-optic construction in DE 100 23 051 A1, in which an external light source is used. Instead of an individual light source, it is also possible to use a plurality of light sources, for example redundant light sources for emitting one and the same wavelength, and/or a plurality of different light sources for emitting different wavelengths. Generally, the at least one light source is intended to be designed to irradiate the body surface with at least one interrogation light.

In this case, in the context of the present invention, an interrogation light is understood to be a light that can be used for the detection of the indicator substance in the sense of the above definition, which light excites the indicator substance inside a body tissue and/or a body fluid, for example with variable penetration depth, to bring about a perceptible response, more particularly an optically perceptible response. This excitation can take place for example in such a way that a luminescence, more particularly a fluorescence and/or a phosphorescence, is excited in the indicator substance. Alternatively or additionally, however, some other type of excitation can also take place, for example scattering of the light at an identical or shifted wavelength. Generally, at least one response light is generated in this response of the indicator substance.

In this case, the interrogation light is intended to be designed in such a way that the desired response is excited in a targeted manner in the indicator substance. Accordingly, by way of example, a wavelength and/or a wavelength range of the interrogation light and/or some other property of the interrogation light can be adapted. This can be done directly by the radiation source, for example, by virtue of said radiation source for example already providing interrogation light having the desired wavelength and/or in the desired wavelength range and/or by virtue of at least one excitation filter additionally being used which filters out the desired interrogation light from a primary light of the light source. In this case, it is particularly preferred if the sensor plaster is designed to perform fluorescence measurements on the indicator substance. Accordingly, the interrogation light can be adapted to an excitation range of this fluorescence of the indicator substance. If a fluorescence of FITC is excited, for example, then it is possible to use interrogation light in the spectral range around 480 nm, for example interrogation light having a perceptible intensity in the range of between 470 nm and 490 nm.

The sensor plaster furthermore comprises at least one detector designed to detect at least one response light incident from the direction of the body surface. The response light can once again be light in the sense of the above definition. The detector, too, can in turn be an integral constituent of the sensor plaster. The detector is therefore part of the sensor plaster, such that the response light is detected directly within the plaster, in contrast for example to the fiber-optic construction in DE 100 23 051 A1, in which an external detector has to be used.

The response light represents the optical response of the indicator substance to the incidence of the interrogation light. Accordingly, the detector and/or the detector in interaction with at least one response filter can be designed to detect in a targeted manner in the spectral range of the response light. In this case, the detector and/or the detector in interaction with the at least one response filter can be designed to suppress light outside the spectral range of the response light. More particularly, the detector and/or the detector in interaction with the at least one response filter can be designed to suppress interrogation light. The interrogation light and the response light can be configured, in particular, such that they are spectrally different or spectrally shifted relative to one another, that is to say different with regard to their spectral intensity distribution.

In particular, the response light can be shifted toward longer wavelengths in comparison with the interrogation light, which is generally the case for example in a fluorescence measurement. By way of example, the spectral shift of a peak wavelength of the response light relative to a peak wavelength of the interrogation light can be between 10 nm and 100 nm, more particularly between 30 nm and 50 nm, and particularly approximately 40 nm. The detector and/or the detector in interaction with the at least one response filter can accordingly be designed to detect such response light. With the use of FITC, by way of example, the detector and/or the detector in interaction with the at least one response filter can be designed to detect response light having a measurable intensity in the range of between 510 nm and 530 nm, in particular at 520 nm.

The at least one radiation source, more particularly the at least one light source, and the at least one detector are designed to irradiate the body surface with the interrogation light and to detect at least one response light incident from the direction of the body surface. The radiation source and the detector are therefore optically connected to the body surface in such a way that, through the body surface, for example transcutaneously, the interrogation light can be radiated into the body tissue or the body fluid and that, likewise through the body surface, for example once again transcutaneously, the response light from the body tissue or the body fluid can be picked up by the detector. The proposed sensor plaster thus differs for example from lab-on-a-chip systems, more particularly from microfluidic systems, which require a sampling system and generally a complex microchannel structure.

The transcutaneous measurement according to the invention can be effected, for example, by the radiation source and/or the detector bearing directly and areally on the body surface. By way of example, the radiation source can comprise an emission surface which can be placed onto the body surface directly or with the interposition of one or a plurality of transparent layers. Accordingly, the at least one detector can comprise at least one sensor surface which can be applied to the body surface for example directly or with the interposition of one or a plurality of transparent layers and via which the interrogation light can be emitted and the response light can be picked up.

In principle, numerous types of radiation sources can be used for the proposed sensor plaster. In this case, it is particularly preferred if the at least one radiation source is configured as a large-area radiation source, that is to say as a radiation source having a radiation-emitting area, for example a light-emitting area, in contrast for example to point light sources or point radiation sources. By way of example, large-area light sources having a light-emitting area of at least 0.2 cm$^2$, preferably at least 0.5 cm$^2$ and particularly preferably 1 cm$^2$ or more of light-emitting area can be used.

It is particularly preferred if the at least one radiation source comprises at least one light source comprising an organic light-emitting material, more particularly an organic light-emitting diode (OLED). In this case, an organic light-emitting material can be understood to mean, in principle, any organic material of natural and/or synthetic origin which is able to emit light. Consequently, this term of OLED also encompasses bio-organic light-emitting diodes, for example. In this case, the generation of light in the organic material can be based on various mechanisms. Thus, by way of example, electroluminescence can be utilized, that is to say excitation of the organic material to emit light by means of an electric current. However, other mechanisms are possible, in principle, for example bioluminescence or other mechanisms. A combination of different mechanisms for generating light is also conceivable.

Alongside the organic light-emitting materials and the corresponding light-emitting layers, further materials and/or functional layers can be provided, for example charge carrier transport layers, barrier layers or similar materials and layers. In this case, purely organic components can be used, that is to say components which exclusively comprise organic light-emitting materials and organic functional layers, or hybrid components can also be used, that is to say components which comprise both inorganic and organic light-emitting materials and/or functional layers. Both shall be encompassed hereinafter by the term of an organic light-emitting diode.

With regard to the construction of organic light-emitting diodes, reference can be made, for example, to the constructions known from the prior art. By way of example, reference can be made to the organic light-emitting diodes described in the above-cited publication by A. Pais et al., or the prior art concerning OLEDs cited in said document.

Organic materials used can be, for example, low molecular weight organic materials, that is to say monomers and/or oligomers, for example. As an example of such low molecular weight substances, reference can likewise be made to the substances used in the abovementioned publication by A. Pais et al. Alternatively or additionally, it is also possible to use polymer materials, for example conjugated polymers. Typical polymer materials of this type that can be mentioned, include, for example, fluorenes or polyphenylene vinylene derivatives (PPVs). Depending on their processing properties, the organic materials can be deposited for example from the gas phase or else from the liquid phase, for example by means of a spin-on method or a printing process. Organic light-emitting diodes are distinguished by the fact that large-area, homogeneously emitting light sources by means of which a large region of the body surface can be irradiated can be produced using this technology.

As an alternative or in addition to the complete or partial configuration of the light source as a light source comprising organic light-emitting material, the at least one detector can also be configured wholly or partly as an at least partly organic detector. Thus, the at least one detector can comprise at least one detector comprising at least one organic semiconducting material, more particularly an organic photodetector (OPD).

With regard to organic photodetectors, too, which can be configured for example wholly or partly as an organic solar cell and/or as an organic photodiode, reference may largely be made to the literature. Thus, by way of example, with regard to possible configurations of the organic photodetector, reference may once again be made to the above-cited publication by A. Pais et al. Once again, it is possible to use fully organic components, or it is also possible to use hybrid components comprising a combination of organic and inorganic materials and/or functional layers. Once again, it is possible to use low molecular weight organic substances, that is to say monomers or oligomers, or, alternatively or additionally, once again also polymers. With regard to possible deposition methods or production methods for the organic components, too, reference may at least largely be made to the above description.

Analogously to the above-described advantages of organic light-emitting diodes, OPDs also have similar advantages. Thus, with this technology, it is possible to produce large-area, thin photodetectors which, similarly to OLEDs can be integrated directly into the sensor plaster. By way of example, it is possible overall to use a layer technology in which the sensor plasters are constructed layer by layer. In this way, sensor plasters having at least two different layer planes can be produced in a layer design. One of said layer planes can be, for example, the at least one flexible carrier element, and others of said layer planes can comprise for example electronic components, for example the detector and/or the radiation source.

Alongside the at least one detector and the at least one radiation source, the sensor plaster can comprise further elements. Thus, the sensor plaster can comprise for example at least one interface for data exchange. Said data can be for example measurement results, for example intensities of the response light that was detected by the detector. Data already partly processed, for example filtered or partly or completely evaluated data, can also be transmitted via said interface. The interface can be configured as a wireless interface, in particular, and can comprise a radiofrequency coil, in particular. In this respect, a transponder technology known from the prior art can also be used, for example, in order to initiate a measurement by means of the sensor plaster and/or to interrogate measurement data from the sensor plaster. Corresponding radiofrequency readers such as are known from RFID technology (radiofrequency identification label technology), for example, can be used for this purpose.

Furthermore, the sensor plaster can comprise at least one driving electronic unit. Said driving electronic unit can be configured, for example, for driving the at least one radiation source and the at least one detector, for example for starting an emission of the interrogation light and/or for initiating a detection of the response light. For this purpose, the driving electronic unit can comprise for example corresponding drivers for the detector and/or the radiation source. A timing for a measurement can also be predefined, such that, for example, the driving electronic unit can predefine a specific time scheme for the radiation source and/or the detector, said time scheme allowing a temporal sequence of the emission of the interrogation light and the detection of the response light. By way of example, the driving electronic unit can be designed to carry out or to control a temporally resolved measurement of the sensor plaster. In this case, a measurement comprises the emissions of at least one interrogation light, more particularly of at least one pulse of the interrogation light, and the detection of at least one response light, more particularly of at least one pulse of the response light. A temporally resolved measurement can accordingly be understood to mean a measurement in which, in addition, a time of the detection of the response light also plays a part or is registered. Thus, by way of example, for each value of the response light, it is also possible to register the corresponding points in time at which this value is recorded and/or it is possible for the response light only to be recorded at specific points in time (gating). In this way, by means of temporally resolved measurements, for example, it is possible to obtain information about a depth from which the respective response light originates, for example by means of propagation time measurements. Alternatively or additionally, it is also possible to use complex measurement schemes in which, for example, the response light is detected at a predefined point in time after the excitation by the interrogation light.

Furthermore, the driving electronic unit, likewise alternatively or additionally, can also be designed to carry out partial or complete processing of the measurement results. In particular, in this case it is possible to process the signals recorded by the at least one detector, and optionally additional information such as, for example, time information, for example the points in time at which the measurement signals of the detector were recorded. The measurement values or measurement signals of the detector can be, for example, intensities of the response light and/or signals of electrical type which correlate with said intensities. In this case, by way of example, complete or partial processing of these signals can be effected, such that, for example, filtering, smoothing, averaging or the like is already effected in the driving electronic unit. Alternatively or additionally, an evaluation of these signals can also already be effected at least in part, for example a determination of a waveform and/or of a half-life and/or a determination of an indicator substance concentration corresponding to these signals.

Partial or complete storage of the information in the sensor plaster, more particularly in the driving electronic unit, is also conceivable. Said information can comprise, for example, one or a plurality of detector signals or information derived therefrom, time information, information about the interrogation light, for example an intensity of the interrogation light, or combinations of said information and/or further information. In order to store the information, the sensor plaster, more particularly the driving electronic unit, can comprise for example one or a plurality of data storage devices, more particularly volatile and/or nonvolatile data memories. Generally, the driving electronic unit can be configured wholly or partly using electrical components, wherein one or a plurality of data processing units, for example microprocessors and/or ASICs, can also be used.

The driving electronic unit can also be configured wholly or partly as organic electronics. Thus the driving electronic unit can comprise for example at least one organic component, that is to say a component comprising at least one organic material, more particularly an active organic material. By way of example, organic conductors and/or semiconductors can be involved in this case. The organic component can comprise for example an organic field effect transistor or simply an organic conductor track.

Organic components of this type are known for example in the form of polymer electronics from DE 10 2004 048 864 A1. By way of example, it is possible to produce organic field effect transistors using organic semiconductor materials which can be part of the driving electronic unit. Simpler organic components can also be encompassed, such as, for example, simple conductor tracks and/or connection contacts which comprise an organic conductive material, for example a conductive polymer. The advantage of such driving electronic units constructed fully or partly using organic technology is once again that such driving electronic units can be produced in flat, small fashion and cost-effectively, such that they can also be used in disposable articles such as plasters, for example. Once again it is possible to use simple and cost-effective layer designs for producing the driving electronic unit, for example printing techniques or the like. Generally, the sensor plaster can preferably be produced using a roll-to-roll technique in which numerous sensor plasters are produced as tape products.

Generally, it is particularly preferred if the driving electronic unit is configured such that it is robust and insusceptible to faults. Thus, by way of example, the driving electronic unit can be configured for enabling an adjustment and/or a calibration. By way of example, corresponding adjustment elements that enable an adjustment can be provided in the driving electronic unit. By way of example, this can involve settable adjustment elements and/or elements which allow trimming. This last can be effected for example by adjustment elements which can be set to the desired properties by means of a suitable trimming process, for example a mechanical trimming method and/or a laser trimming. A trimming to variable properties is also possible, in principle, for example a trimming to a variable wavelength of the interrogation light and/or of the response light. By way of example, a length of an adjustment element can be set by means of such a trimming process.

Furthermore, the driving electronic unit can also be configured in a different way in order to enable repeatable measurement situations. Thus, the driving electronic unit can, for example, be configured in redundant fashion and contain one or a plurality of elements in multiple fashion, for example in order to compensate for a failure and/or a malfunction of one of these elements. Furthermore, it is also possible to use calibrated components, for example calibrated amplifiers, calibrated analogue-to-digital converters, calibrated radiation sources, calibrated detectors or the like. Furthermore, it is possible to use fault-tolerant circuits, redundant circuits and/or compensatory circuits which can ensure a functionality. Furthermore, it is also possible to implement test circuits which, for example, can internally store parameters required during a calibration and make it possible for the sensor plaster, more particularly the driving electronic unit, itself to be reconfigurable. In this way, it is possible to circumvent defective elements, for example, it is possible to set load resistances, or the like.

Furthermore, the proposed sensor plaster can comprise at least one filter element. Said filter element can be used in the beam path of the interrogation light, and said filter element can also be used in the beam path of the response light, and both possibilities can be realized in combination. Thus, by way of example, it is possible to use at least one filter element in the beam path of the response light, that is to say at least one response filter, and/or at least one filter element in the beam path of the interrogation light, that is to say at least one excitation filter. In this case, the at least one response filter and the at least one excitation filter can have different spectral properties, for example different peak transmissions. The at least one excitation filter and the at least one interrogation filter can be configured as separate components or can also be configured wholly or partly as a common component. Furthermore, a configuration in which a filter element is provided only in one of said beam paths is also conceivable.

The at least one filter element can be utilized, for example, to spectrally separate the interrogation light from the response light. By way of example, the interrogation light and the response light can be configured such that they are spectrally different, for example spectrally shifted at least in part relative to one another. In this way, by way of example, in front of the detector it is possible to employ a filter element which at least partly prevents interrogation light from passing into the detector and forming a disturbing measurement background and/or background there. Conversely, by way of example, alternatively or additionally, in front of the radiation source, it is possible to employ a further filter element, which filters out from the spectrum of the radiation source, which spectrum can be configured in broadband fashion, for example, only a specific spectral range for the interrogation light. Various combinations are conceivable.

In principle, all filter elements having spectrally separating properties can be used as the filter element. Interference filters, dichroic mirrors, absorption filters or the like shall be mentioned here as an example. It is particularly preferred if the at least one filter element comprises at least one filter film, that is to say a thin flexible element. Said filter film can be adhesively bonded and/or printed onto the remaining layers using layer technology, for example. A combination of a plurality of filter films is also conceivable. The at least one filter element can also be integrated wholly or partly in the radiation source and/or the detector. By way of example, it is possible to use a radiation source with an integrated excitation filter and/or a detector with an integrated response filter.

Furthermore, the sensor plaster can comprise at least one imaging system, that is to say a system having at least one properties refracting the light, that is to say the interrogation light and/or the response light. In this way, by way of example, the interrogation light can be focused onto a specific body region and/or the response light from a body region can be focused onto the detector. In order to enable a configuration of the imaging system which is as simple as possible, saves as much space as possible and is as cost-effective as possible, it is particularly preferred if said imaging system comprises at least one Fresnel lens. Lenses of this type can be produced for example using printing and/or embossing technology, for example by the corresponding Fresnel structures being embossed into a transparent plastic film. The film embossed in this way can be applied, for example by adhesive bonding, onto the remaining layers of the sensor plaster beforehand or after this treatment.

Furthermore, it is particularly preferred if the sensor plaster comprises at least one electrical energy storage device. Said at least one electrical energy storage device makes it possible for the sensor plaster to be able to be operated autonomously, without having to produce a wireless or wire-based connection for transmission of electrical energy to some other component. However, in principle, such connections are alternatively or additionally likewise possible. In this case, the at least one electrical energy storage device should be configured such that it is as flat as possible and preferably flexible. Accordingly, said at least one electrical energy storage device can comprise a polymer battery, for example. Various configurations are conceivable.

As an alternative or in addition to the use of an electrical energy storage device, however, it is also conceivable for the electrical energy required for the operation of the sensor plaster to be provided in some other way. Thus, by way of example, electrical energy can be radiated in externally, as generally takes place in the case of RFID labels, for example. Once again alternatively or additionally, energy can also be drawn from the surroundings in some other way, for example in the form of heat and/or light. Such devices which draw energy in any form from the surroundings of the sensor plaster and provide the energy as electrically usable energy for the operation of the sensor plaster are referred to hereinafter as an energy generating device. Accordingly, the sensor plaster can optionally comprise one or a plurality of such energy generating devices. Thus, by way of example, the sensor plaster can contain at least one of the following devices: a thermoelement, more particularly a Seebeck element and/or a Peltier element, for converting thermal energy into electrical energy; a solar cell for converting light into electrical energy; a piezoelement for converting mechanical energy, more particularly from vibrations, into electrical energy. Combinations of the aforementioned and/or other types of energy generating devices can also be used.

If, by way of example, a solar cell is used as an energy generating device and/or as part of said energy generating device, then said solar cell can for example in turn be constructed wholly or partly as an organic solar cell. With regard to possible configurations, reference may largely be made to the description of the detector. In contrast to the detector, however, the solar cell is then arranged in such a way that an active area of the solar cell does not face the body surface, for example the skin surface, but rather a direction from which, in a state in which the sensor plaster has been applied on the body surface, generally light incidence of ambient light, more particularly insolation, is to be expected. Thus, by way of example, on a side of the carrier element which faces away from the active area of the radiation source and/or of the detector, the sensor plaster can comprise one or a plurality of solar cells, more particularly organic solar cells, which can provide electrical energy to the sensor plaster applied to the body surface. This provision can be effected directly to the detector, to the radiation source, to the driving electronic unit or to other electrical components of the sensor plaster, or the electrical energy can be temporarily stored, for example once again in one or a plurality of electrical energy storage devices, more particularly polymer batteries. Various configurations are conceivable.

As explained above, the sensor plaster overall is preferably produced wholly or partly in a layer design and comprises at least two different layer planes. Such a layer design enables an integrated construction of high integration density. At the same time, cost-effective techniques can be used. In particular, one or more of the following elements can be produced wholly or partly in a layer design: an optical unit comprising the at least one radiation source and the at least one detector; an electronic unit comprising the driving electronic unit; a communication unit comprising the interface; a sensor module comprising the optical unit, the electronic unit and the communication unit. Various techniques can be used for producing a layer construction, for example lamination techniques, embossing techniques, adhesive-bonding techniques, printing techniques or combinations of the aforementioned and/or other techniques. It is particularly preferred if the radiation source and/or the detector are at least partly applied to the carrier element by means of a printing technique. Accordingly, such a method for producing the sensor plaster is proposed. Other components of the sensor plaster, for example one or more of the components mentioned above, can also be produced by means of the printing technique. As an alternative or in addition to the printing technique, which can comprise, for example, offset printing, screen printing, inkjet printing, pad printing, flexographic printing or a combination of the aforementioned and/or other types of printing, it is also possible to use other layer technologies, for example stamping techniques, embossing techniques or the like. In particular, the polymer electronics which can optionally be encompassed in the driving electronic unit, for example, can also be produced in this way.

Alongside the sensor plaster, a sensor system for the transcutaneous measurement of an organ function, more particularly of a kidney function, is furthermore proposed. The sensor system comprises at least one sensor plaster in accordance with one or more of the embodiments described above. Furthermore, the sensor system comprises at least one reader designed to interact with the sensor plaster, wherein an interaction with a plurality of sensor plasters is also possible. In this case, an interaction can generally be understood to mean a functional interaction in which, for the purpose of the transcutaneous measurement of the organ function, control signals and/or information are exchanged between the reader and the at least one sensor plaster. In particular, the reader can be designed to initiate a measurement of the organ function by means of the sensor plaster. Alternatively or additionally, the reader can also be designed, for example, to receive information from the sensor plaster, for example the information presented above. The reader can be configured as a standing unit or, preferably, as a portable unit. In order to initiate the organ function, by way of example, at least one interface can be present, for example at least one wireless and/or one wire-based interface by means of which, for example, a measurement, comprising the emission of interrogation light and the detection of response light, can be started. The term initiation should likewise be understood to encompass processes in which an emission of interrogation light or a detection of response light is effected permanently, for example, in which case only the respective other of said functions is initiated by the reader.

The reader can comprise for example a radiofrequency transmitter (RF transmitter), for example a radiofrequency transmitter such as is usually used in RFID technology. Said radiofrequency transmitter can be designed to interact with the above-described optional radiofrequency coil of the sensor plaster, for example by the frequencies of these elements being tuned to one another. A unidirectional and/or bidirectional exchange of data and/or control commands can be effected in this way. The radiofrequency transmitter can therefore constitute the interface between the reader and the sensor plaster and/or form a constituent of said interface.

The sensor system can also be configured in a more complex manner. Thus, by way of example, the sensor system can be designed to carry out a plurality of measurements at different points in time, wherein point measurements or else continuous measurements can be encompassed. This implementation of measurements at different points in time can, in particular, also be effected automatically. Furthermore, the sensor system can be designed to determine a temporal concentration profile of an indicator substance in a body tissue and/or a body fluid from the measurement results of said measurements. In this case, the temporal concentration profile can be understood to mean, for example, the complete or piecewise profile of the concentration, or it is also possible, alternatively or additionally, to determine other variables or parameters which characterize the concentration profile. As examples of such variables, the half-life can be mentioned, although other variables can also be used alternatively or additionally. Such variables are referred to hereinafter generally as parameters derived from the concentration profile.

In this case, the indicator substance can be configured as in the above description of the prior art. In particular, the indicator substance can comprise an endogenous and/or an exogenous indicator substance. In this way, for example a clearance of the indicator substance, for example a renal clearance, can be determined by means of the proposed sensor system. In this case, the measurement results can directly reflect the concentrations, or the measurement results can be variables that correlate with the concentrations, for example fluorescence measurement results, the intensity values of which can be proportional to the concentration of the indicator substance in the body tissue and/or the body fluid. Other configurations are also conceivable.

In order to determine the concentration profile of the indicator substance, the measurement results can simply be stored, for example. For this purpose, by way of example, one or a plurality of volatile and/or nonvolatile data memories can be provided in the sensor plaster and/or the reader. By way of example, the measurement results can be stored as measurement value pairs in said memory, for example in the reader. Thus, each measurement value pair can comprise for example a point in time of the measurement (for example indicated in arbitrary or absolute time units) and one or a plurality of associated measurement values of the at least one detector, for example a measured photovoltage at a photodiode of the detector. This detection means, therefore, that the measurement results or the measurement value pairs can be compiled and provided for subsequent interrogation. Alternatively, or additionally, however, it is also possible for the measurement results already to be at least partly conditioned in the sensor system. Thus, by way of example, the sensor system can be designed to represent the concentration profile, for example on one or a plurality of displays of the sensor system, more particularly of the reader. A user can therefore directly identify the profile. Alternatively or additionally, it is also possible for the measurement results already to be at least partly analyzed in the sensor system, such that, for example, elimination half-lives, clearance or similar results which can be determined from the concentration profile can already be fully or partly determined in the sensor system. For this purpose, the sensor system can comprise one or a plurality of correspondingly designed data processing units for example in the sensor plaster and/or the reader. The sensor system can also interact with one or a plurality of further systems, for example one or a plurality of external data processing units. For this purpose, the sensor system can, for example, in turn have a wire-based and/or wireless interface by means of which, for example, the measurement data or measurement results can be interrogated by means of a personal computer, a server or similar computer systems. In this way, a further-reaching evaluation can take place in an external computer system, or, for example, a treating physician can have access to the measurement results.

Alongside the sensor plaster and the sensor system comprising the sensor plaster, a kit for the transcutaneous measurement of an organ function is furthermore proposed. The organ function can be, more particularly, once again a kidney function. The kit comprises at least one sensor plaster in accordance with one or more of the embodiments described above. Alternatively or additionally, the kit can also comprise a complete sensor system in accordance with one or more of the embodiments described above. In this respect, for the possible configurations overall reference may be made to the above description. The sensor plasters can be packaged for example individually or as a plurality, for example in a primary package. The remaining constituents of the kit can be contained, for example together with use instructions, in a further package, which can also comprise the sensor plasters.

Furthermore, the kit comprises at least one indicator substance. Said indicator substance is intended to be able to be introduced in the body of a patient, for example by an injection, by being taken orally, by a transdermal administration or by a rectal administration. In this respect, the indicator substance is intended to have, in particular, the corresponding compatibilities with the organism of a human or animal patient whose organ function is intended to be measured.

Furthermore, the indicator substance is intended to be chosen in such a way that its temporal concentration profile in the body of the human or animal patient, more particularly in a body tissue and/or a body fluid, can be used or can serve as an indicator for the organ function. By way of example, the body fluid can be blood, urine or preferably interstitial fluid.

An indicator substance whose concentration profile can be used as an indicator for the organ function should be understood to mean, in particular, an indicator substance whose concentration is dependent at least substantially, preferably completely, only on the organ function to be observed. If, by way of example, a kidney function, more particularly a glomerular filtration rate, is examined, then the indicator substance used is preferably any desired substance which is substantially exclusively filtered and is not secreted tubularly in significant amounts, nor resorbed back from the primary urine, nor metabolized in the body.

In this case, the indicator substance is intended to comprise at least one marker designed to emit the at least one response light upon incidence of the at least one interrogation light from the radiation source of the sensor plaster. As explained above, a plurality of active mechanisms for the emission of the response light can be considered here. In particular, these mechanisms can be luminescence, more particularly fluorescence and/or phosphorescence. However, other mechanisms are also possible, in principle, for example light scattering, for example Raman and/or Stokes scattering. In principle, other mechanisms are also possible, for example absorption and/or reflection, preferably wavelength-dependent absorption and/or reflection. In this respect, the response light can comprise for example a reflective, a transmitted or a scattered light beam or a combination of such light beams. Alternatively or additionally, the response light can also comprise a fluorescent light and/or a phosphorescent light or a response light that arises in some other way during the interaction of the interrogation light with the marker.

In this case, the marker can likewise be configured in different ways. Thus, firstly, the indicator substance as a whole can be configured as such a marker, such that, for example, spectroscopic properties, that is to say corresponding to one or more of the above-described active mechanisms for the interaction with the interrogation light, of the entire molecule or of all molecules of the indicator substance can be interrogated by means of the interrogation light. Alternatively or additionally, however, the indicator substance can also merely comprise the marker as one of a plurality of constituents. Thus, by way of example, one or a plurality of marker radicals, marker groups or similar marker constituents can be coupled to the indicator substance by means of bonding. By way of example, this can involve covalent bonding, complex bonding, ionic bonding or else simple bonding by means of Van-der-Waals forces. The marker can comprise for example a fluorescent molecule, for example fluorescein isothiocyanate (FITC) described above.

The indicator substance according to the invention is therefore preferably a fluorescent-marked indicator substance. The latter preferably has a structure according to the general formula (I):

$$P—F \qquad (\text{formula I})$$

where P is a polyol; and
where F is a marker having optically measurable properties, more particularly a fluorescent and/or phosphorescent marker.

Polyols for the indicator substance preferably comprise polyethylene glycol, ethylene glycol, propylene glycol, glycerol, mannitol, sorbitol, hexitols, pentitols, tetritols, inositols, mannose, aldoses, lactose, cellobiose, gentiobiose, β-alkyl glycosides, deoxy sugar, β-alkyl uronic acids, fucose, deoxy sugar alcohols, fructose, and respective derivatives, wherein the polyol is present as deoxyamino sugar alcohol. The polyol is preferably a polysaccharide, particularly preferably inulin or sinistrin and more particularly an inulin or mixture of inulins comprising from 3 to 20, preferably 11 to 15 or 3 to 8, fructose units.

The marker is preferably selected from the group consisting of: fluorescein dyes, cyanine dyes, naphthyl amide dyes, coumarin dyes, xanthene dyes, thioxanthene dyes, naphtholactone dyes, azlactone dyes, methine dyes, oxazine dyes, thiazine dyes. F is preferably a fluorescein dye, particularly preferably fluorescein.

The fluorescent marker can preferably be bonded to the polysaccharide by means of a coupling group. Suitable coupling groups and coupling reactions are known to the person skilled in the art. Particularly preferably, the coupling group is selected from the group consisting of: thiourea group (—N—CS—N—), thiocarbamate group (—N—CS—O—), carbamate (urethane) group (—N—CO—O—), ether group (—O—), thioether group (—S—), ester group (—CO—O—), amide group (—CO—N—), thioester group (—CS—O—), thioamide group (—CS—N—), amino alkyl group (—CO—N—(CH$_2$)n-O—) where n=2 to 5, secondary amine group (—NH—). In particular, the fluorescent marker is present as fluorescein isothiocyanate (FITC).

Such substances can be used more particularly for the kidney function measurement, as well as other indicator substances which are eliminated exclusively via the urinary tract in the human body. The use of fluorescence-marked polysaccharides and/or cyclosaccharides such as, for example, sinistrins and/or fructosans which are marked with FITC, for example, is particularly preferred. For the production of such marked polysaccharides and/or cyclosaccharides, reference may be made for example to the above prior art, for example WO2001/85799 or WO2006/32441.

Alongside the sensor plaster, the sensor system or the kit, in each case in one or more of the embodiments described above, the use of one or more of these devices for a transcutaneous measurement of an organ function is furthermore proposed. More particularly, this can involve a kidney function, more particularly a glomerular filtration rate.

A method for the transcutaneous measurement of an organ function is correspondingly proposed, more particularly of a kidney function. This method can be carried out more particularly using a sensor plaster and/or a sensor system and/or a kit in accordance with one or more of the embodiments described above, such that, for possible configurations of the method, reference may largely be made to the above description.

The method comprises the following steps, which preferably, but not necessarily, are carried out in the order presented below. Additional method steps (not presented) can also be carried out and/or individual or a plurality of the method steps can be carried out temporally in parallel, in a temporally overlapping manner or else repeatedly.

In a first method step, a sensor plaster is applied, more particularly stuck, onto a body surface. The sensor plaster comprises at least one radiation source, preferably as an integral constituent, wherein the radiation source is designed to irradiate the body surface with at least one interrogation light. The sensor plaster furthermore comprises a detector, preferably likewise as an integral constituent, which is designed to detect at least one response light incident from the direction of the body surface.

In a further method step, at least two temporally delimited measurements at different points in time and/or at least one continuous measurement over a time period are carried out, wherein the response light is detected at the different points in time and/or over the time period. In this respect, it is possible to form for example once again, as described above, measurement value pairs in which one point in time is assigned one or a plurality of measurement values of the detector, for example corresponding sensor signals. The detection can likewise be effected in accordance with the above description, such that, for example, storage and/or provision of said measurement value pairs can be effected.

In a third method step, a temporal profile of a concentration of an indicator substance is then deduced from a temporal profile of the response light. In this case, the temporal profile of the response light may be known continuously or in a pointwise manner. Thus, as explained above, the temporal profile can be measured continuously, for example. Alternatively or additionally, however, an extrapolation and/or interpolation of individual measurement values can also be effected, for example by adaptation of one or a plurality of the measurement curves. By way of example, said adaptation can already be fully or partly effected in the sensor plaster and/or in a reader of the sensor system. Other configurations are also conceivable, for example subsequent external evaluation in a separate computer system.

As explained above, the method is intended to be performed, in particular, in such a way that the response light correlates with the concentration of the indicator substance. In this case, it is possible to utilize for example the above-explained interaction mechanisms between the interrogation light and the indicator substance and/or a marker of the indicator substance, for example a fluorescent mechanism. Since, for example from calibration measurements and/or empirical or semi-empirical or theoretical considerations, a relationship between the concentration of the indicator substance and the response light, for example an intensity of the response light and/or a detector signal of the detector, is known or can be determined, this conclusion drawn from the temporal profile of the response light about the concentration of the indicator substance is easy to realize for the person skilled in the art. By way of example, this conversion into the concentration of the indicator substance can be effected in arbitrary units, such that, for example, the intensity of the response light can be used directly as a measure of the indicator substance. Alternatively or additionally, however, some other type of conversion can also be effected, for example by means of one or a plurality of stored conversion curves, conversion algorithms or conversion tables which, for example, can be used in one or a plurality of data processing units. Thus, by way of example, this conversion can be effected fully or partly in a data processing unit of the sensor plaster and/or in a data processing unit of the reader and/or in a further, external data processing unit.

As explained above, the indicator substance can be an endogenous or exogenous indicator substance. In this respect, this indicator substance can, for example, be present anyway in the body of the human or animal patient and/or can be artificially increased in its concentration for a short time by artificial uptake of the indicator substance, for example by being taken orally, by rectal administration or by injection, in order then to terminate the supply. Alternatively or additionally, it is also possible, for example, to regulate a supply of the indicator substance in such a way that the temporal profile of the concentration of the indicator substance is substantially constant, wherein the corresponding organ function can be deduced from the required replenishment rate, for example measured in quantitative units or mass units per unit time. That, too, is intended to be encompassed by the concept according to the invention that the temporal profile of the concentration of the indicator substance is deduced from the temporal profile of the response light. Various other measurement methods are conceivable. The supply of the indicator substance can correspondingly be part of the proposed method.

Overall, the proposed devices and methods have a large number of advantages, which can be realized individually or in combination, by comparison with known devices or methods of this type. Thus, by way of example, the sensor plaster can be configured as a printable, intelligent sensor sticking plaster based on electronics. It is therefore possible to realize a sensor plaster with low production costs since, for example, printing methods with large-scale printing machines can be used. In this case, it is also possible to use inexpensive raw materials such as, for example, cost-effective organic polymers for the detector and/or the radiation source or light source and/or other constituents of the electronics, for example of the evaluation electronics.

Furthermore, for the detector, the data processing, the storage and the interface or combinations of these and/or other elements, it is possible to use standard elements which can also be used again in other configurations. In this respect, it is possible to realize a modular system, which can likewise in turn lead to reduced production costs, reduced stock-keeping costs and thus overall to a lowering of costs.

The sensor plaster can thus be configured, in particular, as a highly integrated sticking plaster. The dimensions of this sticking plaster can correspond to the dimensions of customary sticking plasters, that is to say for example in the range from 5 to 100 mm×5 to 100 mm. The sensor plaster can be composed of an optical unit in the form of the radiation source, for example a light-emitting diode, a laser or the like, and one or a plurality of detectors, which can likewise be assigned to the optical unit. Said detector can comprise, as explained above, a photodiode and/or a solar cell, for example. The optical unit comprising the radiation source and the detector can be embodied as an independent unit, for example, which can be applied for example also in a spatially continuous fashion on the sensor plaster. This optical unit can be combined for example with one or a plurality of filter films and/or with optical imaging systems produced by pressing technology or printing techniques, for example Fresnel lenses. In this way it is possible to produce an optical unit which operates reliably, is cost-effective and has an extremely small volume and has a high degree of integration.

Alongside the optical unit, an electronic unit can be provided, which can comprise, for example, the evaluation electronics described above. The latter can comprise, for example, suitable amplifiers, converters (for example A/D converters), controllers, storage elements or combinations of the aforementioned and/or other components.

As an alternative or in addition to the electronic unit and alongside the optical unit, the sensor plaster can furthermore comprise one or a plurality of communication units. By way of example, this can involve, as explained above, an RFID-based communication unit. The latter can comprise, for example, one or a plurality of radiofrequency coils. The communication unit can interact functionally with the optical electronic unit and/or the optical unit.

Alongside the optical unit and the optional electronic unit and/or the optional communication unit, the sensor plaster can comprise further elements such as, for example, the electrical energy storage device and/or the energy generating device, such as the solar cell, for example. Other elements can also be encompassed, for example display elements or the like, which makes it possible for a user to exchange information and/or control signals with the sensor plaster.

The construction of the sensor plaster according to the invention can be implemented in a comparatively simple manner. Thus, in each case at least one detector, for example at least one solar cell, and at least one radiation source, for example at least one OLED, can be printed on for example alongside the at least one adhesive surface, for example having two adhesive regions, in the center of the sensor plaster. In each case suitable filter films can be situated in front of said optical elements, which filter films can prevent, for example, interrogation light from being concomitantly detected by the detector to a considerable extent. The driving electronic unit for the optical unit comprising the detector and the radiation source can be situated alongside and/or behind said optical unit. Said driving electronic unit, as explained above, can likewise once again be configured as a cost-effective printed driving electronic unit and can contain a driving system for the detector and/or the radiation source. A device for digitizing the measurement signals, for example the signals generated by the detector, can also be provided. Furthermore, alternatively or additionally, it is also possible to provide one or a plurality of storage elements and/or a control electronic unit for the read-out, for example by means of radiofrequency signals.

Likewise using layer technology it is possible to produce the interface, for example with the radiofrequency coil. The latter can, for example, in turn be produced in an overlying layer plane and can generate radiofrequency signals, which can then be read out. By way of example, the reader can comprise a conventional RFID reader for reading out the radiofrequency signals. This information can then be transmitted by the reader, for example into a suitable database, which can be part of the reader or part of a separate unit. From said database, for example a further evaluation of the measurement signals or measurement results can then be effected later.

The energy required for picking up the measurement signals can be provided wholly or partly by the optional energy storage device, which, for example, can likewise be integrated into the sensor plaster. By way of example, said electrical energy storage device can in turn be constructed fully or partly using polymer technology, for example fully or partly as a polymer battery. By way of example, a printing technique can once again be used for applying said polymer battery. Alternatively or additionally, other types of energy storage devices can also be used, for example conventional thin-film energy storage devices. Once again alternatively or additionally, however, it is also possible to use other energy sources, for example energy sources which are mounted externally and which can be connected to the sensor plaster via one or a plurality of interfaces. Thus, for example, a wireless transmission of energy to the sensor plaster can be effected, and/or a transmission by means of a power supply cable (which can be attached to the sensor plaster, for example).

The carrier material or the at least one carrier element of the sensor plaster can perform further tasks alongside provision of the at least one adhesive area for sticking onto the body surface of the human or animal patient. Thus, the carrier material can be chosen, for example, in such a way that it has substantially light-tight properties, such that, for example, no disturbing stray light, for example ambient light, can pass through the carrier material to the detector and/or to the body surface to be irradiated with the interrogation light. A disturbing stray light background can be suppressed in this way. Furthermore, the sensor plaster, for example the carrier element and for example the adhesive areas thereof, can be configured in such a way that no light, for example ambient light, can penetrate laterally. By way of example, this can be effected by virtue of the fact that the adhesive areas enclose the optical unit, that is to say the detector and/or the radiation source, completely in the plane of the body surface. Penetration of stray light and/or ambient light can likewise be prevented in this way. Furthermore, the adhesive used and/or other materials of the sensor plaster can also be configured in light-tight fashion, that is to say in such a way that they are configured such that they are largely nontransparent or have low transparency to light in the spectral range of the interrogation light and/or the response light.

The sensor system can be put into operation, for example, by a radiofrequency pulse, for example emitted by the reader, initiating or activating the sensor plaster, for example a driving electronic unit of the sensor plaster. The sensor plaster can thereby be excited to record measurement data. Said measurement data can be digitized, for example, and entered into one or a plurality of storage elements. As described above, said one or plurality of storage elements can be configured as measurement value memories, for example as volatile and/or nonvolatile memory, for example as flash-type memory. Said at least one storage element can, for example, likewise be contained in the sensor plaster. In the latter case, these data can then be read out for example by the reader, for example once again by means of radiofrequency technology. Alternatively or additionally, at least partial data processing can also already be effected on the sensor plaster, such that data that have already been at least partly processed can be forwarded to the reader. Once again as an alternative, it is also possible for completely raw data, for example data generated directly by the detector, already to be forwarded to the reader in order to be stored there in one or a plurality of storage elements. Various combinations are conceivable.

In the configuration of the detector and/or the radiation source and/or the evaluation electronics or other electronic components of the sensor plaster, it is possible, as already mentioned in part above, to design the components individually or in groups in such a way that repeatable measurement situations are possible. Thus, it is preferred particularly, as explained above, if calibrated radiation sources, for example calibrated light-emitting diodes and/or lasers, are used. Alternatively or additionally, correspondingly calibrated detectors can also be used. Furthermore, likewise alternatively or additionally, further electronic components can also be configured as calibrated components. By way of example, calibrated amplifiers and/or A/D converters can be used. In order that the measurement situation is further made repeatable, it is also possible to use fault-tolerant and/or redundant electrical circuits which, for example, can also be configured in a compensatory fashion. The functionality can be ensured in this way. Furthermore, it is also possible to use test circuits in order to internally store the required parameters during the calibration and to allow the system to configure itself accordingly. In this way it is possible, for example, to circumvent defective elements, it is possible to set load resistances, or the like. The evaluation circuit can optionally comprise one or a plurality of such test circuits. Overall, the proposed devices can thus be configured in a manner insensitive to interference and enable reliable and reproducible measurements.

In principle, the present invention also relates to the use of a fluorescence-marked indicator substance for the production of a diagnostic aid for determining the glomerular filtration rate (GFR).

The fluorescence-marked indicator substance used according to the invention in this connection is preferably a polysaccharide, particularly preferably inulin or sinistrin and, more particularly, a mixture of inulins comprising from 3 to 20, preferably 11 to 15 or 3 to 8, fructose units, wherein the inulins are coupled to a fluorescent marker. The fluorescent marker is preferably selected from the group consisting of: fluorescein dyes, cyanine dyes, naphthyl amide dyes, coumarin dyes, xanthene dyes, thioxanthene dyes, naphtholactone dyes, azlactone dyes, methine dyes, oxazine dyes, thiazine dyes. F is preferably a fluorescein dye, particularly preferably fluorescein.

The fluorescent marker can preferably be bonded to the polysaccharide by means of a coupling group. Suitable coupling groups and coupling reactions are known to the person skilled in the art. Particularly preferably, the coupling group is selected from the group consisting of: thiourea group (—N—CS—N—), thiocarbamate group (—N—CS—O—), carbamate (urethane) group (—N—CO—O—), ether group (—O—), thioether group (—S—), ester group (—CO—O—), amide group (—CO—N—), thioester group (—CS—O—), thioamide group (—CS—N—), amino alkyl group (—CO—N—(CH$_2$)n-O—) where n=2 to 5, secondary amine group (—NH—). In particular, the fluorescent marker is present as fluorescein isothiocyanate (FITC).

Preferably, the inulin mixture can be obtained by enzymatic digestion and subsequent chromatographic separation of naturally occurring inulin. By means of enzymatic digestion using a β-glucosidase, preferably inulinase [E.C.: 3.2.1.7], and the subsequent chromatography, mixtures of inulin having a degree of polymerization (i.e. number of saccharide monomer units in the polysaccharide) of between 3 and 20 and preferably between 3 and 8 or 11 and 15 can be provided in a targeted manner. Depending on the constitution of the starting material, corresponding inulin mixtures can also be obtained just by chromatographic separation.

The fluorescence-marked indicator substance is formulated as a diagnostic aid according to the invention. In this case, a defined quantity sufficient to generate a detectable fluorescent signal after administration is dissolved in a physiologically tolerated solvent, e.g. water or aqueous salt solutions, PBS, etc., and if appropriate admixed with physiologically tolerated auxiliaries, e.g. stabilizers. It goes without saying that the quantity of fluorescence-marked indicator substance can differ depending on the use of the diagnostic aid and depending on the subject to be examined. Factors that can play a part in this connection are body weight, age, sex, type and extent of the kidney dysfunction or presumed kidney dysfunction, and/or medical history. A diagnostic aid within the meaning of the present invention can finally also contain indications concerning the type, duration, extent and side effects of the use, which can be enclosed in the form of an instruction leaflet or in electronic form, e.g. on a data carrier. Furthermore, the instruction leaflet or the data carrier can contain indications that allow an interpretation of the GFR.

The term of glomerular filtration rate (GFR) has already been defined in detail elsewhere in the description. The determination of the GFR preferably serves, according to the invention, for diagnosing existing kidney dysfunctions, for determining the risk of future progression of the kidney dysfunctions, for monitoring in the case of diseases, therapeutic interventions or therapies which can cause kidney dysfunctions, or for determining the individual dose for medicaments that are excreted via the kidney. Kidney dysfunctions should be understood to mean all pathological alterations of the kidney function which result in a changed and preferably decreased, but also increased, GFR. These preferably include chronic kidney dysfunctions and acute kidney failure, but also hyperfiltration and e.g. in the case of poorly controlled diabetes mellitus. However, kidney dysfunctions can also be brought about as secondary disturbances resulting from other diseases. Thus, kidney dysfunctions can also occur in the presence of cardiovascular diseases or when there is a predisposition for the occurrence of cardiovascular diseases and in the case of diabetes mellitus order renalis.

Depending on the purpose of determining the GFR, the diagnostic aid can be administered as a bolus or by infusion. Accordingly, different aspects of the GFR can be measured such as the so-called input clearance, infusion clearance or bolus clearance.

Advantageously, the diagnostic aids disclosed here are suitable for the noninvasive, transcutaneous measurement of the GFR. The fluorescence-marked indicator substances penetrate after administration into the interstitial space, where a nondisruptive determination of the fluorescence after excitation is possible. The determination is preferably effected using a device as disclosed elsewhere in the description, but can also be effected using other methods and devices known in the prior art for the quantification of fluorescent substances. A further advantage of the diagnostic aids used according to the invention is that the fluorescent-marked indicator substance consists of a defined mixture of polysaccharides, more particularly inulins. This allows a standardization of the GFR determination, which was problematic previously since although inulin is the gold standard for determining the GFR, it has disadvantages with regard to standardization on account of a changing composition. Through the use of smaller polymers it is additionally possible to increase the solubility in particular in water and aqueous solutions. Precipitation problems, which also consequently lead to clinical side effects, can likewise be avoided. By virtue of the increased solubility, it is additionally possible to administer smaller volumes as diagnostic aid, which additionally increases the biocompatibility. Through the use of smaller polymers, moreover, an optimum degree of marking with the fluorescence marker relative to the overall molecule is also achieved, which makes it possible to reduce the quantity of fluorescence-marked indicator substance in the diagnostic aid. Therefore, less indicator substance has to be administered, since the fluorescence marking occurs more frequently in the same volume.

Finally, by virtue of the ratio of marker to polymer in the fluorescence-marked indicator substances that are to be used as a diagnostic aid according to the invention, the lipophilic properties of said substances is also increased. As a result, the renal excretion rate is reduced and the half-life in the organism is increased.

Finally, the invention also relates to a method for determining the glomerular filtration rate (GFR), comprising the following steps:
a. administering a fluorescence-marked indicator substance, preferably a mixture of inulins, as explained above, to a subject;
b. measuring the fluorescence noninvasively on the body surface; and
c. determining the GFR on the basis of the measurement values from step b.

The method according to the invention is preferably carried out noninvasively. The device according to the invention can be used for this purpose. However, other systems known in the prior art for fluorescence measurement can also be used. As has already been explained, the GFR can be determined—depending on the further purpose of use—as input clearance, infusion clearance or bolus clearance. Accordingly, the administration can be effected as bolus provision, as infusion or as a mixed form. The measurement can also be a single measurement (determination of the fluorescence at one specific point in time) or a repeated measurement (determination of the fluorescence at a plurality of points in time for profile representation).

The GFR can be determined in relative or absolute fashion. Within the meaning of the present invention, relative determination should be understood as the determination of a change, i.e. of an increase or decrease in the GFR. This can, if appropriate, also be expressed as a percentage change from an initial value. The determination of the absolute GFR presupposes that firstly a calibration for the indicator substance is carried out, which allows a specific concentration of indicator substance in the blood, plasma or serum to be assigned to a specific measured fluorescence value. On the basis of this concentration, the GFR can then be calculated using the formulae known in the prior art.

The method can be partly automated. As already mentioned, the devices of the present invention can be used for the measurement. The evaluation and calculation of the GFR can be effected in a computer-aided manner.

In one preferred embodiment of this method, a diagnosis can also be made on the basis of the GFR. A statistically significantly reduced GFR is preferably an indicator for a kidney dysfunction or a predisposition therefor. A statistically significant reduction of the GFR can also be an indicator for lowering the dosage of medicaments that are excreted via the kidney. Conversely, an increased GFR can be an indicator that no kidney dysfunction or predisposition therefor is present. The increased GFR also indicates the need to increase the dosage of medicaments that are excreted via the kidney. Such diagnostic evaluations of the GFR determined by the method according to the invention can, of course, also be effected in an automated manner, e.g. by using a diagnostic algorithm implemented on a computer.

The sensor plaster or sensor system according to the invention and the kit according to the invention can also be used for the transcutaneous measurement of an organ function, which presuppose a functioning barrier between blood vessel system and extravasal spaces. Preferably, it is possible to use sensor plasters, sensor systems or kit for the transcutaneous measurement of the intestinal wall barrier function or the blood-brain barrier function. In this case, the barrier function can be determined by determining the increase or decrease in fluorescence-marked indicator substance in the blood. It goes without saying here that an intensified decrease in the fluorescence-marked indicator substance in the blood will occur in the case of a disturbed barrier function. Conversely, an increase in fluorescence in the blood is possible after oral administration of the fluorescence-marked indicator substance in the presence of a barrier disorder.

The invention therefore also relates to a method for the transcutaneous measurement of the intestinal wall barrier function or of the blood-brain barrier function, more particularly using a sensor plaster (116) as claimed in any of the preceding embodiments relating to a sensor plaster (116) and/or a sensor system (114) as claimed in any of the preceding embodiments relating to a sensor system (114) and/or a kit (110) as claimed in any of the preceding embodiments relating to a kit (110), wherein the method comprises the following steps:
a sensor plaster (116) is applied, more particularly stuck, onto a body surface, wherein the sensor plaster (116) comprises at least one radiation source, wherein the radiation source is designed to irradiate the body surface with at least one interrogation light (162), wherein the sensor plaster (116) furthermore comprises a detector (146), wherein the detector (146) is designed to detect at least one response light (176) incident from the direction of the body surface;
at least two temporally delimited measurements at different points in time and/or at least one continuous measurement over a time period are carried out, wherein the response light (176) is detected at the different points in time and/or over the time period; and
a temporal profile of a concentration of an indicator substance (112) is deduced from a temporal profile of the response light (176).

Preferably, the mixture according to the invention of inulins or an FITC inulin or an FITC sinistrin is used in the abovementioned methods or uses.

However, the invention also relates to the use of a fluorescence-marked indicator substance and preferably of the mixture according to the invention of inulins or of an FITC inulin or of an FITC sinistrin for the production of a diagnostic aid for diagnosing dysfunctions of the intestinal wall barrier or of the blood-brain barrier.

In this case, the occurrence of dysfunctions of the intestinal wall barrier is preferably connected with the occurrence of Crohn's disease or ulcerative colitis, such that the abovementioned uses and methods can be used, in principle, for diagnosing these diseases.

Dysfunctions of the blood-brain barrier occur in connection with various hereditary diseases, but can also be connected with other diseases, e.g. neurodegenerative diseases, inflammations of the CNS or stroke. Hereditary diseases with disorders of the barrier function of the blood-brain barrier that are taken into consideration preferably include GLUT1 deficiency syndrome, hereditary folate malabsorption or biotin-responsive basal ganglia disease.

Sensor plasters, sensor systems or kit according to the present invention can also be used for determining the pancreas function. In this case, the function of the arylesterases of the pancreas is determined by transcutaneous measurement of the increase in fluorescence in the blood. In this case, the fluorescence originates from enzymatically released fluorescein, for example, which originates from fluorescein dilaurate which can be administered as substart of the arylesterases to the subject to be examined. Similar substrates that can be used for determining the pancreas function include fluorescence-marked triglyceride analogues or a nitrophenyl ester of a fluorescence-marked alkylphosphonate. A more detailed description of such substrates is found in Scholze 1999, Analytical Biochemistry 276:72-80 or Negre-Salvayre 1990, Lipids 25 (8): 428-434. Reference is hereby expressly made to the substrates disclosed therein.

Consequently, the invention also relates to a method for the transcutaneous measurement of the pancreas function, more particularly using a sensor plaster (116) as claimed in any of the preceding embodiments relating to a sensor plaster (116) and/or a sensor system (114) as claimed in any of the preceding embodiments relating to a sensor system (114) and/or a kit (110) as claimed in any of the preceding embodiments relating to a kit (110), wherein the method comprises the following steps:

- a sensor plaster (116) is applied, more particularly stuck, onto a body surface, wherein the sensor plaster (116) comprises at least one radiation source, wherein the radiation source is designed to irradiate the body surface with at least one interrogation light (162), wherein the sensor plaster (116) furthermore comprises a detector (146), wherein the detector (146) is designed to detect at least one response light (176) incident from the direction of the body surface;
- at least two temporally delimited measurements at different points in time and/or at least one continuous measurement over a time period are carried out, wherein the response light (176) is detected at the different points in time and/or over the time period;
- a temporal profile of a concentration of an indicator substance (112) is deduced from a temporal profile of the response light (176), wherein the indicator substance is fluorescein dilaurate, a fluorescence-marked triglyceride analogue or a nitrophenyl ester of a fluorescence-marked alkyl phosphonate.

EXEMPLARY EMBODIMENTS

Further details and features of the invention will become apparent from the following description of preferred exemplary embodiments. The exemplary embodiments are illustrated schematically in the figures. In this case, identical reference symbols designate elements which are identical or functionally identical or correspond to one another in terms of their functions.

The invention is not restricted to the exemplary embodiments.

Specifically in the Figures:

FIGS. 7A to 7D show clearance experiments with F5 and F10 inulin fractions and sinistrin.

Example 1

Measurement Set-Ups

Figure 1:
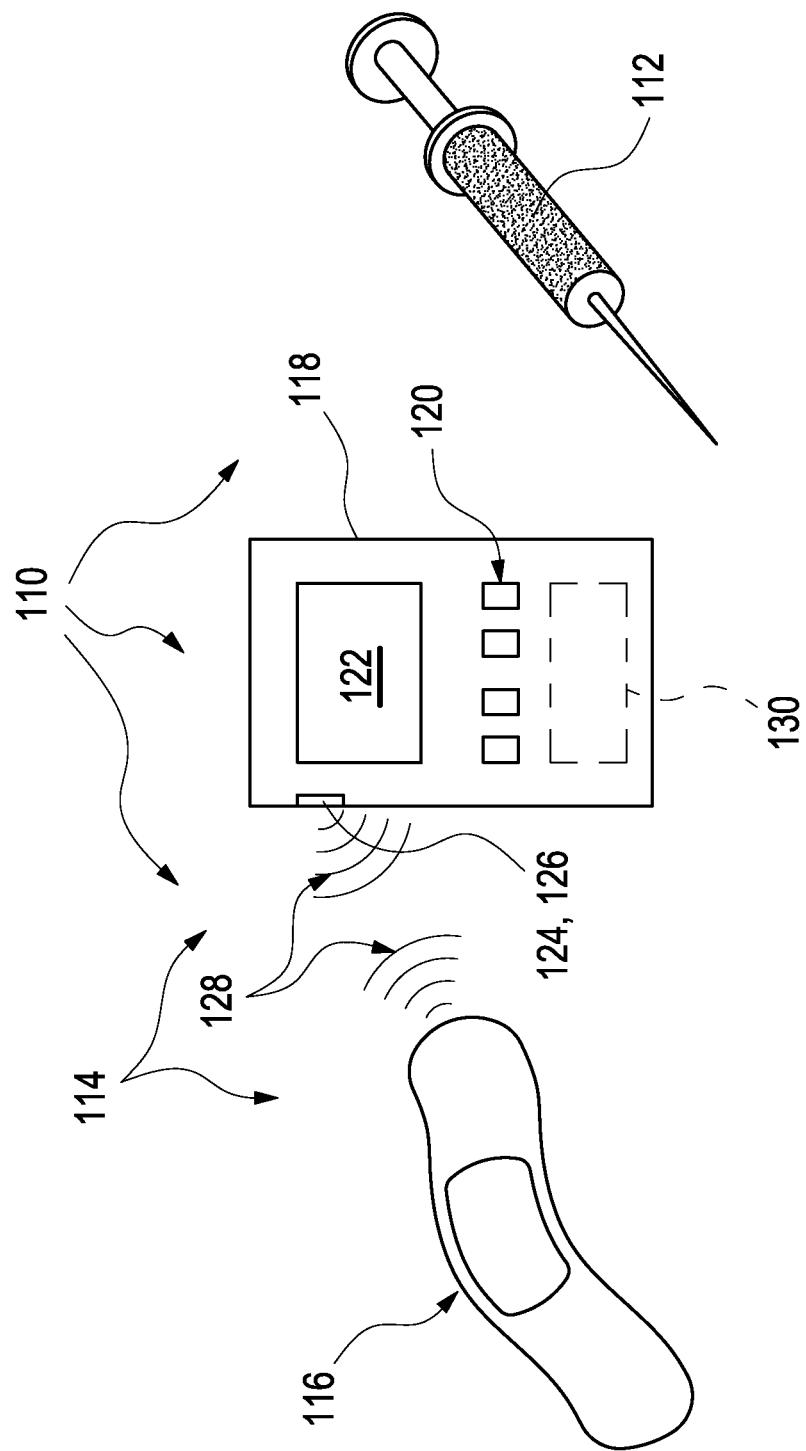
FIG. 1 shows an exemplary embodiment of a sensor system and kit according to the invention for the transcutaneous measurement of an organ function.

An exemplary embodiment of a kit 110 according to the invention for the transcutaneous measurement of an organ function is illustrated highly schematically in FIG. 1. In this exemplary embodiment, the kit 110 comprises an indicator substance 112, which here is illustrated symbolically as the content of a syringe. As an alternative or in addition to an injection of said indicator substance 112, however, other types of administration are also taken into consideration, for example oral, transdermal or rectal administrations. Furthermore, it is also possible to have recourse to endogenous indicator substances. Accordingly, the kit 110 can comprise suitable forms of administration for said indicator substance 112, for example syringes, ampoules, tablets, bags, small tubes or the like.

Alongside the indicator substance 112, the kit 110 in the exemplary embodiment illustrated comprises a sensor system 114 for the transcutaneous measurement of an organ function. The sensor system 114 comprises a sensor plaster 116 for the transcutaneous measurement of an organ function, said sensor plaster merely being indicated symbolically in FIG. 1. Furthermore, the sensor system 114 comprises a reader 118, which is likewise shown highly schematically. The reader 118 can comprise one or a plurality of input and output means, for example, which are illustrated symbolically in the form of operating elements 120 in FIG. 1. Furthermore, the reader 118 can comprise one or a plurality of indicator elements 122, for example one or a plurality of displays, acoustic indicator elements or the like, for example in order to convey measurement results or other information to a user.

Furthermore, the reader 118 can comprise one or a plurality of interfaces 124, for example a radiofrequency interface 126, for communication with the sensor plaster 116. Alternatively or additionally, further interfaces 124 can be provided, for example wire-based interfaces, for example likewise for communication with the sensor plaster 116 and/or with further electronic equipment, for example an external computer system. Wireless communication by means of radiofrequency electromagnetic radiation is designated symbolically by the reference numeral 128 in FIG. 1. As indicated in FIG. 1, this communication 128 can take place bidirectionally or can also take place just unidirectionally.

Furthermore, as indicated in FIG. 1, the reader 118 can comprise a driving and evaluation electronic unit 130. This driving and evaluation electronic unit 130 can comprise for example one or a plurality of electronic components, for example a data processing unit, one or a plurality of volatile and/or nonvolatile memories and other components.

Figure 2:
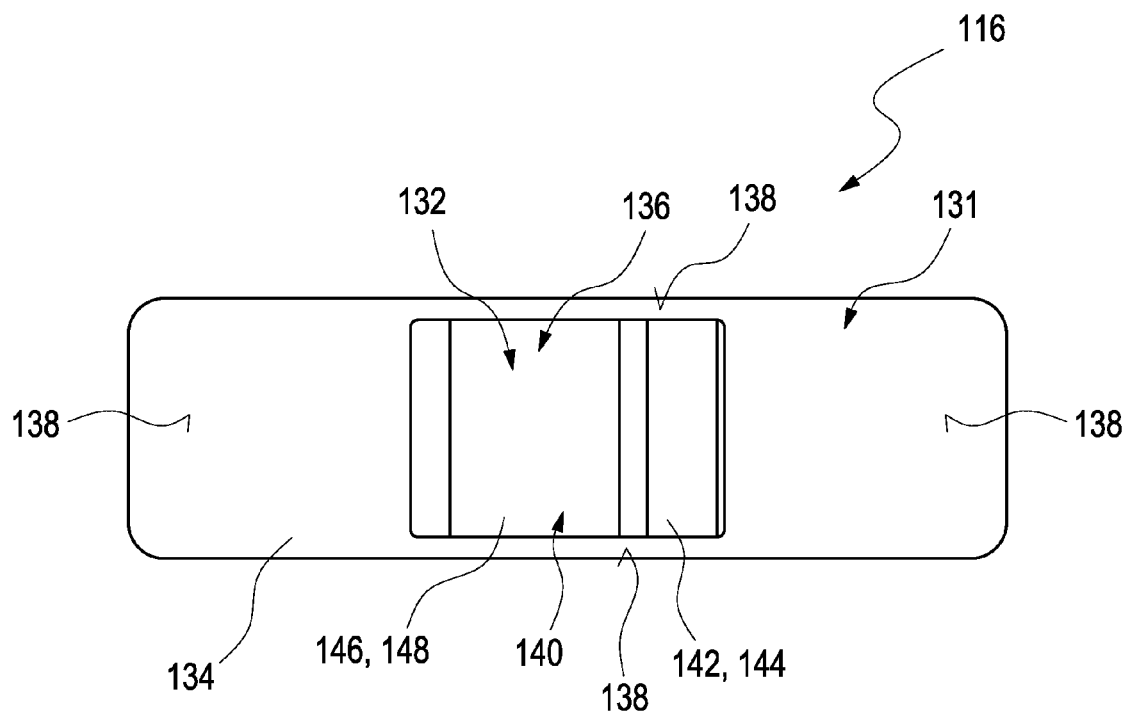
FIGS. 2A and 2B show an exemplary embodiment of a sensor plaster according to the invention in different illustrations.
Figure 2:
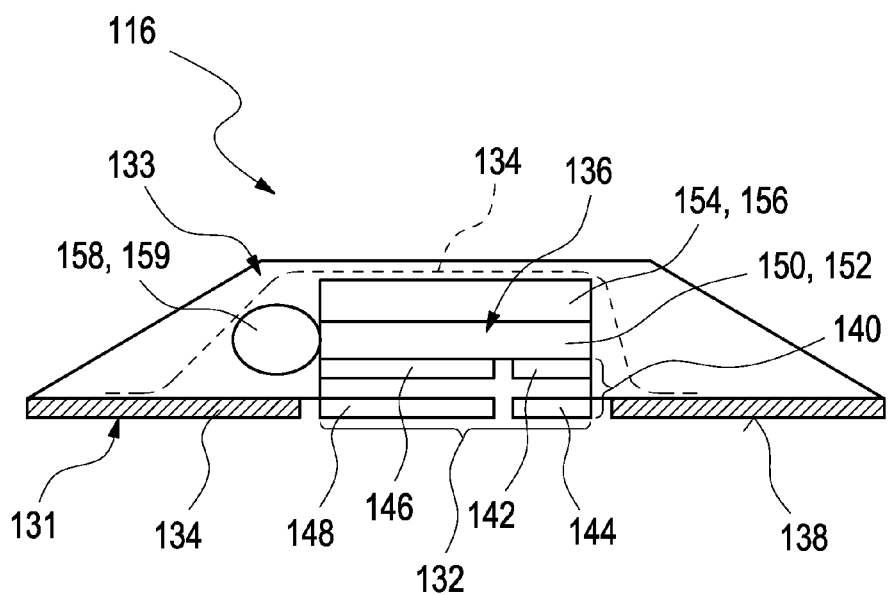

FIGS. 2A and 2B illustrate a schematic illustration of possible exemplary embodiments of a sensor plaster 116 according to the invention in different viewing directions. The sensor plaster 116 has a front side 131, which, in a state in which the sensor plaster 116 has been applied to a body surface (not illustrated in the figures), faces the body surface, and a rear side 133 facing away from the body surface. In this case, FIG. 2A shows a plan view of the front side 131 of the sensor plaster 116, whereas FIG. 2B shows a perspective view of the sensor plaster 116 highly schematically. In this perspective view, however, a layer construction is indicated symbolically, in a departure from the perspective illustration. The front side 131 is at the bottom in the illustration in accordance with FIG. 2B.

As emerges from the plan view of the front side 131 of the sensor plaster 116 in accordance with FIG. 2A, the sensor plaster 116 comprises a flexible carrier element 134. Said flexible carrier element 134 can be configured in light-tight fashion, for example, and can serve as a carrier for the actual sensor module 136. By way of example, the flexible carrier element 134 can be configured in the form of a rectangular, elongate strip and can comprise for example a carrier material comprising at least one flexible material and/or a layer construction of such flexible materials. By way of example, it is possible here to use plastic materials, ceramic materials, paper materials, glass materials or combinations of the aforementioned and/or other materials.

The carrier element 134 is intended to be configured flexibly in such a way that it can be deformed in such a way that an adaptation to the respective body surface on which the measurement is intended to take place is possible. In this respect, the term "flexible" should be interpreted as "deformable" in the context of the present invention.

As indicated by the dashed line in FIG. 2B, the carrier element 134 can completely cover the sensor module 136 on the rear side 133. However, just partial covering is also possible, in principle, for example if the sensor module 136 additionally comprises (see below) a solar cell, having a solar cell area facing toward the rear side 133.

The sensor module 136 has at least one active area 132 facing the front side 131 and thus, in the applied state of the sensor plaster 116, the body surface. Said active area 132 can also be configured in the form of a plurality of individual areas. The active area 132 can comprise for example one or a plurality of light-emitting areas of at least one light source 142, one or a plurality of detector areas of at least one detector 146, one or a plurality of filters 144, 148, optical elements, protective elements or other components of the sensor module 136 and/or combinations of the aforementioned elements and/or other elements of the sensor module 136.

The carrier element 134 has an adhesive surface 138, which completely encloses the active area 132 in the exemplary embodiment in accordance with FIG. 2A. The adhesive surface 138 can be configured as a self-adhesive adhesive surface 138 by means of an adhesive, for example. In particular, said adhesive surface 138 can in turn be configured in such a way that, when the sensor plaster 116 has been stuck in place, no ambient light can pass to the sensor module 136.

In the exemplary embodiment illustrated, the sensor module 136 has an optical unit 140 as a bottommost—as viewed from the front side 131—element of a layer construction. In the exemplary embodiment illustrated, said optical unit 140, the layer construction of which can be discerned in FIG. 2B, for example, comprises a light source 142, which is configured as an organic light-emitting diode (OLED), for example. An excitation filter 144, for example a filter film, can be applied on said light source 142, such that said excitation filter 144 faces toward the body surface.

In the exemplary embodiment illustrated, the optical unit 140 furthermore comprises a detector 146, for example an organic solar cell. Said detector 146 is provided, on its side facing the active area 132, for example, with a response filter 148, for example once again in the form of a filter film adhesively bonded onto the detector 146.

As can be discerned from FIG. 2A and FIG. 2B, both the light source 142 and the detector 146 are configured as large-area components, such that a large area of said components in each case faces the active area 132 bearing directly on the body surface of the patient. By way of example, both the light source 142 and the detector 146 can have active areas facing the body surface which comprise a few 10 $mm^2$, for example. However, smaller or larger areas are also possible, in principle. In this way, it is ensured that interrogation light is radiated onto the body surface in a large-area manner and response light from the body surface can also be received in a large-area manner. Organic components are particularly well suited to such large-area components since, for example in contrast to conventional inorganic semiconductor components, organic components by their nature are configured in large-area fashion.

In the next layer plane, on that side of the optical unit 140 which faces away from the active area 132, the sensor plaster 116 in the exemplary embodiment illustrated comprises an electronic unit 150. As an alternative or in addition to the example illustrated in FIG. 2B, however, said electronic unit 150 can also be arranged in a different way, for example wholly or partly alongside the optical unit 140. However, the layer construction illustrated can be realized particularly simply in terms of printing technology, for example, and brings about short electronic transmission paths and also a flat and compact design. The electronic unit 150 can comprise for example a driving electronic unit 152 for the driving and/or evaluation of the optical unit 140. By way of example, by means of this driving electronic unit 152, the light source 142 can be excited to emit interrogation light and/or the detector 146 can be excited to detect response light. Furthermore, the driving electronic unit 152 can also comprise one or a plurality of data storage devices in order to perform at least buffer-storage of the measurement results that were obtained by means of the detector 146. Various other configurations are possible.

Furthermore, the sensor plaster 116 in accordance with the exemplary embodiment illustrated in FIGS. 2A and 2B comprises a communication unit 154, which can be configured for example wholly or partly as an interface 156 for communication with the reader 118. Said communication unit 154 can be configured using RFID technology, for example, and/or can comprise a radiofrequency coil in order to realize the wireless communication with the reader 118 as designated symbolically by reference numeral 128 in FIG. 1. The communication unit 154, too, can be driven wholly or partly by the driving electronic unit 152 and/or can have a separate driving electronic unit 152.

Furthermore, the sensor plaster 116 in the exemplary embodiment illustrated in FIG. 2B comprises an electrical energy source 158. While the communication unit 154, the electronic unit 150 and the optical unit 140 are arranged one above another in a layer design in the exemplary embodiment illustrated in FIGS. 2A and 2B, which, however, likewise need not necessarily be the case, the electrical energy source 158 is arranged alongside this layer construction in FIG. 2B. Alternatively or additionally, however, the at least one electrical energy source 158 can also be integrated fully or partly into the layer construction of the units 140, 150 and 154.

The electrical energy source 158 can comprise for example a printed battery, for example a printed polymer battery. The electrical energy source 158 can supply one or a plurality of the units 140, 150 and 154 with electrical energy. As explained above, however, as an alternative or in addition to the at least one electrical energy source 158, the sensor plaster 116 can also comprise one or a plurality of energy generating devices, which are designated symbolically by the reference numeral 159 in FIG. 2B. Said energy generating devices 159 can, as indicated symbolically in FIG. 2B, be configured jointly with the electrical energy source 158, but can also be embodied wholly or partly spatially separately from said electrical energy source 158.

By way of example, the required electrical energy can be radiated in externally, in the manner used in conventional transponder technology. For this purpose, by way of example, the communication unit 154 can receive its energy required for communication with the reader 118 from the incident electromagnetic waves. Alternatively or additionally, the energy generating device 159 can also comprise for example one or a plurality of solar cells, for example once again one or a plurality of organic solar cells. This at least one solar cell can then comprise for example at least one solar cell area which faces the rear side 133 of the sensor plaster 116 and which is preferably at least not completely covered by the carrier element 134, such that incidence of ambient light, more particularly sunlight, onto said solar cell area is possible. Once again alternatively or additionally, the energy generating device 159 can comprise one or a plurality of thermoelectric converters, for example one or a plurality of Peltier or Seebeck elements. Other configurations are also possible, or else combinations of the aforementioned and/or other possibilities for the configuration of the energy generating device 159.

Figure 3:
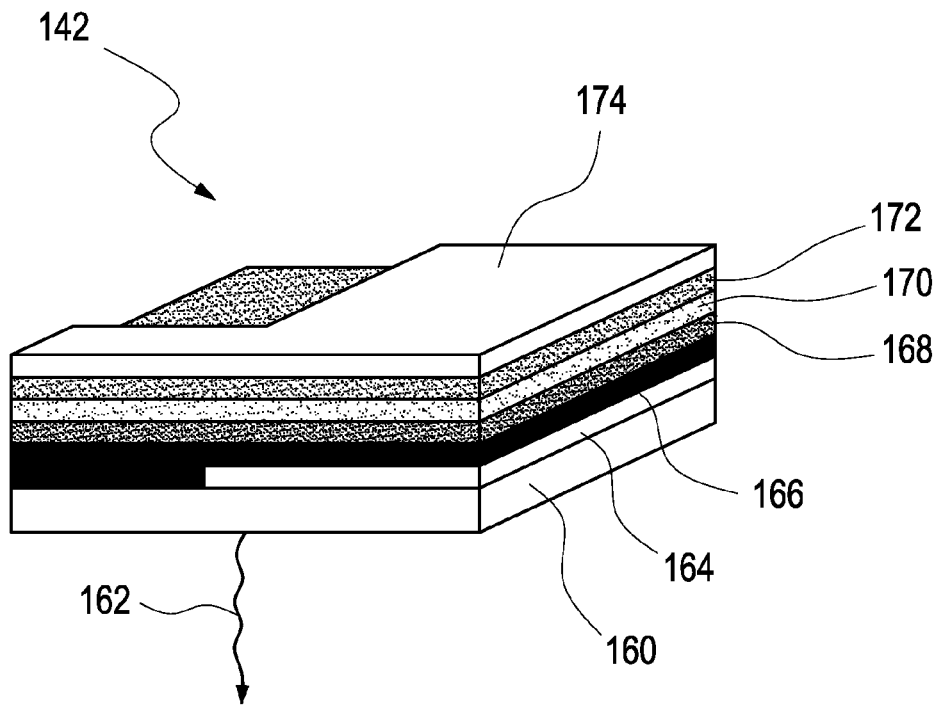
FIG. 3 shows an exemplary embodiment of an organic light-emitting diode that can be used in the sensor plaster.
Figure 4:
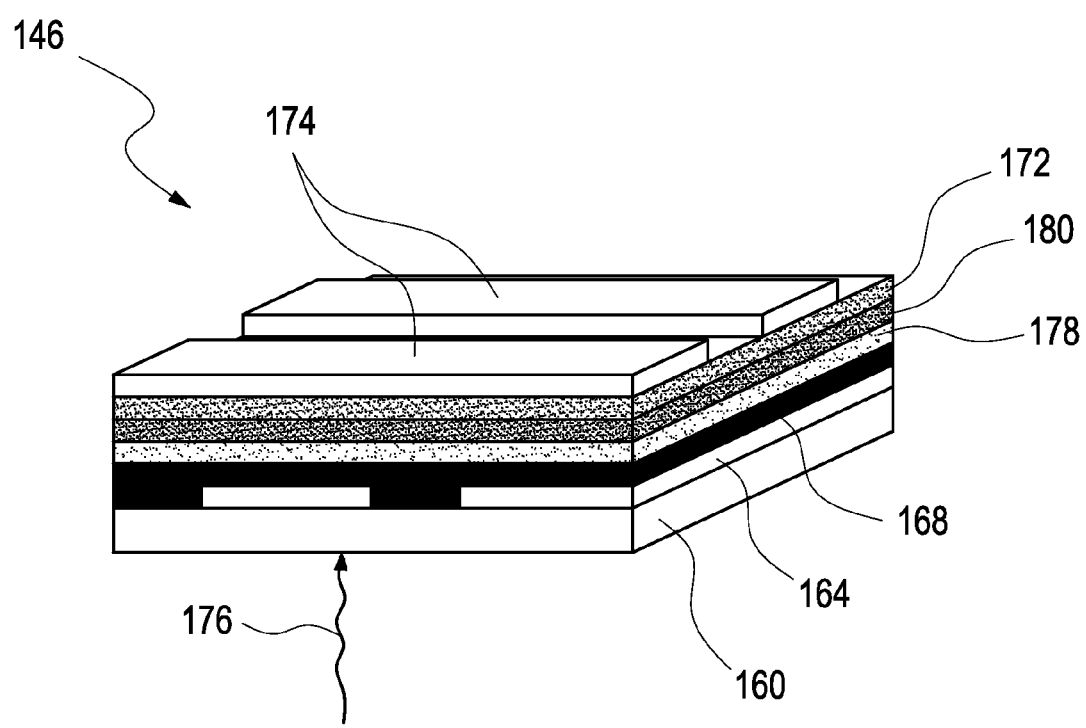
FIG. 4 shows an exemplary embodiment of an organic solar cell that can be used in the sensor plaster.

FIGS. 3 and 4 show possible exemplary embodiments of the light source 142 (in FIG. 3) and of the detector 146 (in FIG. 4) in schematic perspective illustration. It should be pointed out that these layer constructions are merely examples of a multiplicity of possible layer constructions, and that materials other than those illustrated, other layer sequences, other layer thicknesses, other geometries or other types of production of the layers can also be used.

The light source 142 firstly comprises a substrate material 160. In the exemplary embodiment illustrated in FIG. 3, said substrate material 160 is configured as transparent substrate material through which the interrogation light 162 generated by the light source 142 can leave the light source 142. In this respect, in the case of the layer construction in accordance with FIG. 2B, said substrate material 160 has to face the active area 132. It should be pointed out that, in order, for example, to be able to print the layer sequence of the light source 142 directly onto the remaining layers of the layer construction illustrated in FIG. 2B and/or to be able to print it directly onto the carrier element 134, the substrate material 160 can also be dispensed with or that said substrate material 160 can be replaced by a different type of transparent material. Such constructions are often also referred to as inverse constructions since, in the case of such constructions, the layer sequence of the light source 142 is not actually applied to the substrate material 160 in the order illustrated, but rather in the opposite order. The designation "upside-down" layer construction is also found in this regard.

A transparent anode 164 is applied on the transparent substrate material 160, which can comprise for example a glass, for example a thin, flexible glass, or optionally a transparent plastic material or a combination of these and/or other materials. Optionally, a different electrode than the anode can also be configured as a transparent electrode. By way of example, indium tin oxide (ITO), for example having a layer thickness of 30 to 80 nm, for example 50 nm, can be used as transparent anode material.

A barrier layer 166 can be applied to said transparent anode 164, which barrier layer can also be configured as a whole injection layer. By way of example, this can be an oxide layer, having a thickness in the range of a few nanometers, for example 10 nm. For a possible construction of such a whole injection layer, reference may be made to the above-described publication by A. Pais et al.

A thin layer of a hole transport material 168 is applied to the barrier layer 166. Said hole transport material 168, which has particularly high mobilities for positive charge carriers, for example radical cations, can be for example a layer of a few nanometers, for example 10 to 50 nm, of an N,N'-diphenyl-N,N'-bis(1-naphthyl)(1,1'-biphenyl)-4,4'diamine (NPB). Other hole transport materials or combinations of a plurality of layers of different hole transport materials can also be used.

In the exemplary embodiment illustrated in FIG. 3, a layer of an emitter material 170 is applied on the hole transport material 168. In said emitter material 170, the photons of the interrogation light 162 are generated by positive and negative charge carriers recombining there and/or exciton pairs reacting and emitting photons in the process. By way of example, said emitter material 170 can comprise a layer of a few nanometers, for example 10 to 50 nm, of a tris(8-hydroxyquinoline)aluminum (Alq). Other types of emitter materials or combinations of different emitter materials can also be used.

In the exemplary embodiment illustrated, a layer of an electron injection material is applied to the emitter material 170, said electron injection material promoting electron injection into the emitter material 170 or of an electron transport material (not illustrated in FIG. 3) applied to the emitter material 170. By way of example, said electron injection material 172 can comprise a thin layer of a fluoride, for example lithium fluoride, for example with a layer thickness of 0.5 to 2 nm, more particularly 1 nm. A cathode 174 is then applied to said electron injection material 172, from which cathode electrons are injected into the organic layer construction. By way of example, it is possible to use an aluminum cathode 174 having a layer thickness of 50 to 200 nm, for example 100 nm. Other electrode materials can also be used in principle. If an inverse layer construction is used, in which the interrogation light 162 has to be emitted through the cathode 174, for example on account of the printing problem explained above, then the cathode 174, as an alternative or in addition to the anode 164, can also be configured in transparent fashion. This can be done for example by using thin metal layers, for example in combination with transparent electrode materials such as, for example, once again ITO.

Furthermore, it is indicated in FIG. 3 that the electrodes 164, 174 can be suitably structured, if appropriate, in order to enable contact to be made with said electrodes 164, 174.

The exemplary embodiment illustrated in FIG. 3 is an exemplary embodiment of a light source 142 in which the active layers are produced completely from low molecular weight organic materials. Such low molecular weight organic materials are usually deposited from the gas phase. However, liquid phase deposition is also possible, in principle. It should be pointed out that other materials can also be used, and/or other deposition techniques, for example polymer materials, which can be applied for example by a wet-chemical process. In the latter case, in particular, a printing process or a method in which a plurality of printing processes are used is advantageous.

FIG. 4 shows, likewise only by way of example, an exemplary embodiment of a detector 146 in an illustration analogous to FIG. 3. It should once again be pointed out that other materials, other layer combinations, in particular inverse constructions, constructions comprising additional layers or other types of modifications of the layer construction shown are also possible.

The detector 146 in FIG. 4 is constructed as an organic photodiode. The starting point in the exemplary embodiment illustrated is once again a substrate material 160, which can once again be configured in transparent fashion, for example, such that response light, which is designated by the reference numeral 176 in FIG. 4, can pass through said substrate material 160 into the detector 146. It should once again be pointed out that, in the context of the present invention, inverse constructions can also be used, that is to say constructions in which the response light 176 can pass into the detector 146 through a transparent top electrode (that is to say from above in FIG. 4) without penetrating through the substrate material 160. Such a construction would be preferred for example in the context of a printing method for use in a sensor plaster in accordance with FIG. 2B, in which, for example, the layer sequence shown in FIG. 4 would be printed in an inverse order onto the light-opaque carrier element 134 illustrated in FIG. 2B. The light entrance of the response light 176 could then be effected either via a transparent cathode or via a transparent anode, which would be arranged on that side of the layer construction which faces away from the carrier element 134 and faces the active area 132. In this respect, the statements made in respect of the organic light source 142 in accordance with FIG. 3 are analogously applicable to the detector 146.

In the case of the exemplary layer construction in accordance with FIG. 4, a transparent anode 164 is applied to the transparent substrate material 160, which anode can once again comprise structured ITO for example, which can be applied for example on a thin glass substrate 160 or a thin plastic substrate 160.

A hole transport layer is applied to the ITO of the anode 164, said hole transport layer comprising for example a layer having a thickness of a few 10 nm, for example a layer having a thickness of 50 nm, poly(3,4-ethylenedioxythiophene):polystyrene sulfonate (PEDOT:PSS). This layer fulfills for example functions similar to those of the hole transport material 168 in accordance with FIG. 3, such that the reference numeral 168 has likewise been used for this hole transport layer in FIG. 4.

In the exemplary embodiment illustrated in accordance with FIG. 4, a double layer system of an acceptor-donor system comprising copper phthalocyanine 178 and the buckminsterfullerene $C_{60}$ 180 is applied to said hole transport layer 168. A mixed system in which said layers 178, 180 are intermixed, for example, is also conceivable. While the functional principle of the organic light-emitting diode in accordance with FIG. 3 is based on generation of photons upon recombination of electron-hole pairs (or the organic equivalents thereof), the functional principle of the organic photodiode in accordance with FIG. 4 is based on the opposite effect, in which photons entering into the component generate electron-hole pairs (or the organic equivalents thereof). Finally, the $C_{60}$ layer 180 has applied to it an optional LiF layer 172 and a structured cathode 174, for example an aluminum cathode, in a similar manner to the construction in accordance with FIG. 3.

For further details of the possible exemplary embodiments which can be used in the context of the present invention, reference may be made to the above-described publication by A. Pais et al.

It should furthermore be pointed out that the spectral properties of the components in accordance with FIGS. 3 and 4 can be adapted to the respective requirements of the sensor plaster 116 in a simple manner. Thus, by way of example, the interrogation light 162 of the light source 142 can be adapted to the respective requirements of the indicator substance 112 or of a marker contained in said indicator substance 112. The illustrated component comprising Alq as emitter material emits in the green spectral range, for example. However, it is possible to produce components, for example by doping of the emitter material with suitable dyes and/or by using other emitter materials which emit in other spectral ranges. By way of example, numerous organic light-emitting diodes exist which emit in the short-wave visible spectral range, that is to say for example in the blue spectral range through to the near and ultraviolet spectral range. In this way, the interrogation light 162 can be adapted for example to the respective absorption characteristics of the indicator substance 112 or of a marker of said indicator substance 112. By way of example, emitter materials exist which emit in the blue spectral range. By way of example, various fluorine compounds as polymer materials emit in the blue spectral range. In the case of the low molecular weight emitter materials, spiro compounds, for example, should be mentioned as possible emitters in the blue spectral range. Various other configurations and combinations of different emitter materials are possible.

Analogously, the spectral properties of the detector 146 can also be adapted to the response light 176 to be detected, such that optimum signal generation can be effected. This can be done for example by using a donor-acceptor system that differs from the donor-acceptor system illustrated in FIG. 4. Various configurations are possible. It is also possible, for example, to use a plurality of light sources 142 having different spectral properties and/or a plurality of detectors 146 having different absorption characteristics, such that a simultaneous measurement in a plurality of spectral ranges can also be effected.

Figure 5:
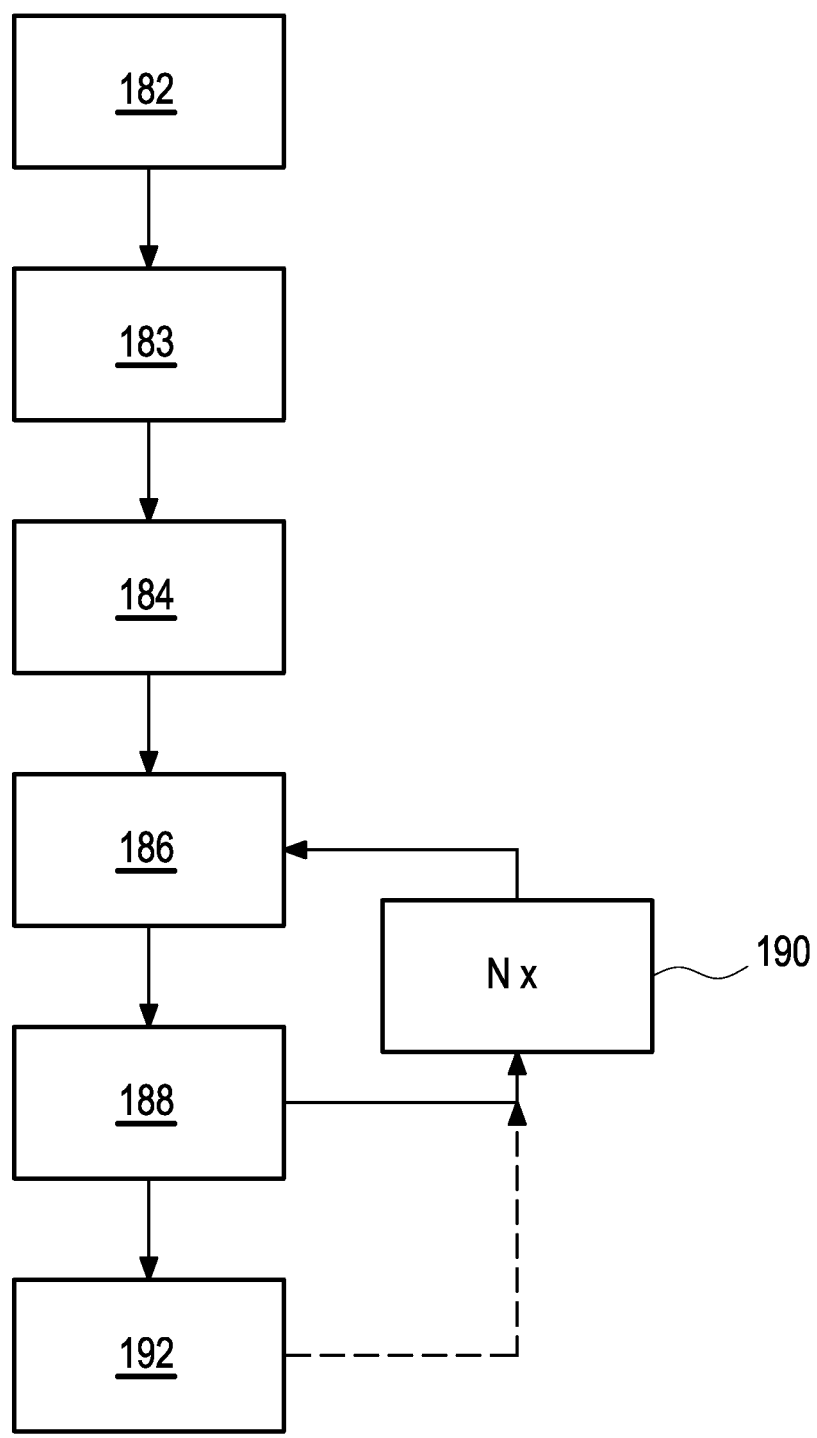
FIG. 5 shows a flowchart of a possible exemplary embodiment of a method according to the invention for the transcutaneous measurement of an organ function.

Finally, FIG. 5 shows an exemplary embodiment of a possible method according to the invention for the transcutaneous measurement of an organ function as a highly schematic flow chart.

The method begins in step 182 with the application of a sensor plaster 116 to a body surface of a human or animal patient. This can be done, for example, by the adhesive surface 138, which can be configured as a self-adhesive adhesive surface, being stuck onto the body surface.

The method step 182 is followed optionally by a step of a zero value measurement, which is designated by the reference numeral 183 in FIG. 5. This method step 183 serves the purpose of determining signals of the sensor plaster 116 before the indicator substance 112 is introduced. This can serve the purpose, for example, of eliminating electronic offsets, background signals or the like, and/or defining a position of the coordinate axes. The results of the zero value measurement 183 can also be used for other purposes. The zero value measurement 183 can be effected, for example, by the step 186 (described below) of a detection being carried out without the indicator substance 112 having been introduced into the body. It is also possible for this method step 186 to be carried out a number of times. Furthermore, it is also possible to carry out additional method steps, for example step 188 (likewise described below) of storing information, for example storing the results of the zero value measurement 183.

Subsequently, in the example of the method according to the invention as illustrated in FIG. 5, there follows a method step 184, in which the indicator substance 112 is introduced into the patient's body. This introduction can be effected, as explained above, for example by being taken orally, by injection or the like. It should be pointed out that this method step 182 need not necessarily be part of the method since, for example, it is also possible to use endogenous indicator substances 112 which are present anyway in the body and the supply of which can be interrupted, for example, or the regeneration of which can be blocked. Various configurations are conceivable.

Method step 186 involves detection of a concentration of the indicator substance 112 in a body tissue and/or a body fluid of the patient by means of a transcutaneous measurement. By way of example, a measurement in interstitial fluid can be involved.

For the purpose of this detection 186, by means of the light source 142, interrogation light 162 is radiated through the body surface into the body tissue or the body fluid, where a corresponding interaction with the indicator substance 112 or a marker of said indicator substance 112 is brought about, such that the response light 176 arises. Said response light 176 is picked up by means of the detector 146. This gives rise to a first measurement signal, for example in the form of a measurement value pair, which can comprise, for example, the point in time of the measurement or detection 186, the measured value of the response light 176 (for example an intensity and/or a variable that correlates with said intensity, for example a photovoltage). Further data can also be contained in said measurement value pair, for example a luminance of the light source 142 or a variable that correlates with said luminance, for example a current through the light source 142.

These measurement results are stored in step 188. This storage can be effected for example in an internal storage device of the sensor plaster 116 or can, alternatively, or additionally, also be effected in a storage device of the reader 118. By way of example, the sensor plaster 116, in particular the electronic unit 150 and/or the communication unit 154, can comprise a volatile or nonvolatile memory, for example a flash memory.

Subsequently, method steps 186 and 188 can be repeated, as indicated by the reference number 190 in FIG. 5. The evaluation 192, which will be explained in greater detail below, can also wholly or partly be a constituent part of the repetition 190, this being indicated by the dashed line in FIG. 5. The repetition 190 can also be effected in such a way that a predefined time is allowed to elapse between the individual repetitions and/or that the repetitions take place at predefined points in time. In this way, by means of an N-fold repetition, a measurement series can be recorded in which the detection 186 takes place continuously or discontinuously over a certain time period, for example at fixed or variable time intervals.

Subsequently, an evaluation is optionally effected in method step 192. This evaluation 192 can be effected in different ways and to different degrees. By way of example, the evaluation can already be wholly or partly performed in the sensor plaster 116, for example in the electronic unit 150, more particularly the driving electronic unit 152. Alternatively or additionally, however, an evaluation can also be effected in the reader 118, there more particularly in the driving and evaluation electronic unit 130, and/or in a separate computer system, which can be connected to the reader 118, for example. A repetition is also possible.

The evaluation can consist, for example, in a smoothing of the measurement results, a filtering of the measurement results, an adaptation of measurement curves (for example in order to determine a half-life), a graphical representation or the like. A combination of the abovementioned steps and/or other evaluation steps is also conceivable. By way of example, the half-life and/or a renal clearance of the indicator substance 112 can be determined as the result of the evaluation 192. Other parameters are also conceivable.

Example 2

Properties of Defined Inulin Mixtures

Defined inulin mixtures comprising 3 to 8 (F5) or 11 to 15 (F10) sugar monomers were obtained from the raw material inulin by digestion with an inulinase and subsequent chromatographic separation into individual fractions.

The chromatographically separated fractions F5 and F10 were derivatized with fluorescein isothiocyanate (FITC) to form FITC-F5 and FITC-F10. FITC-F10 was administered to rats intravenously. The interstitial fluorescence of the FITC measured at an excitation wavelength of 485-520 nm was determined. The fluorescence in the serum was measured as a control.

It was noticeable that with a reduction of the sugar residues the renal excretion rate gradually decreased, with half-lives of 25.98+/−2.66 min for FITC-F10 and 30.3+/−2.2 min for FITC-F5 compared with a half-life of 25.02+/−1.67 min for sinistrin and 23.04+/−1.02 min for FITC-sinistrin and 22.0+/−0.8 min for the unmarked inulin F5 fraction.

The increase in the half-life can at least partly be explained by an increase in the lipophilic properties of the molecules after fluorescence marking. The marking efficiency for the F10 and F5 fractions was, moreover, such that the fluorescence could even still be determined after drastic dose reduction by a factor of 10 or more. The results are illustrated graphically in FIGS. 6A to 6D and 7A to 7D.

Figure 6:
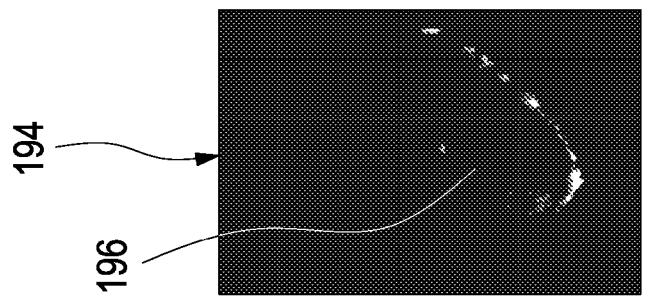
FIGS. 6A to 6D show a detection of fluorescence-marked inulin fractions in the interstitial tissue.
Figure 6:
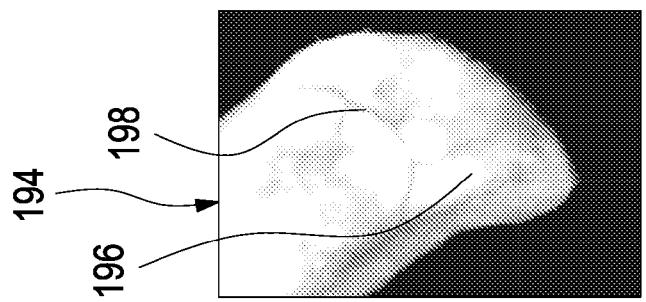
Figure 6:
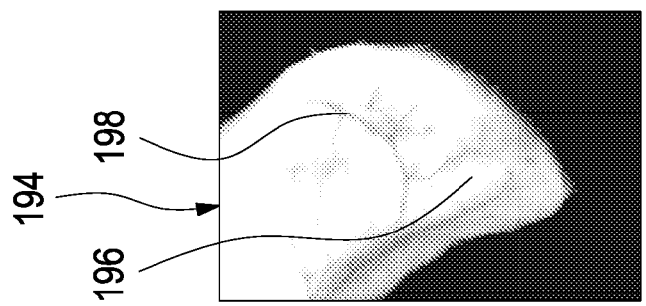
Figure 6:
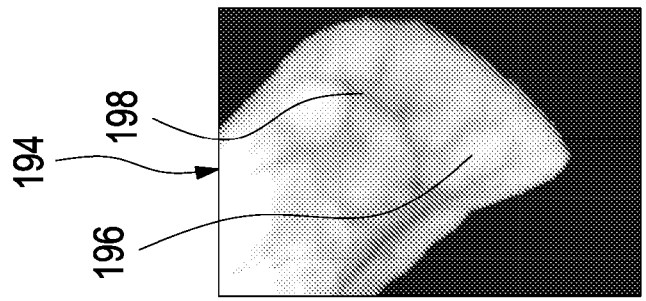

FIGS. 6A to 6D illustrate recordings of a rat ear 194 which were obtained using a small-animal imager of the CRI-Maestro type. The recording times are 0 min (FIG. 6A), 1 min (FIG. 6B), 10 min (FIG. 6C), and 120 min (FIG. 6D). The fluorescent areas, discernible as bright in the figures, correspond to the interstitial space 196 in the tissue. Regions without fluorescence mark the course of blood vessels 198. FITC-marked polyfructosans can therefore be measured transcutaneously in the interstitial space, in principle.

FIGS. 7A to 7D show clearance experiments with FITC-marked polyfructosans which were measured enzymatically or fluorometrically in plasma samples. In all the figures, the relative concentration c in percent is plotted against the time t in minutes. FIG. 7A shows the decrease in the relative concentrations of marked (FITC-S, measurement values represented as rhombi) and non-marked sinistrin (S, measurement values represented as squares) over time. FITC-S was administered to rats as a bolus of 250 mg/kg body weight, and S as a bolus of 750 mg/kg body weight. The half-lives for FITC-S and S are 23.9+/−1.4 min and 22.8+/−1.4 min, respectively.

FIGS. 7B and 7C illustrate the decrease in the relative concentration for FITC-F10 (FIG. 7B) and FITC-F5 (FIG. 7C) over time and compared with that of S (measurement values for FITC-F10 and FITC-F5 are represented as rhombi, and those for S as squares). S was administered to rats as a bolus of 750 mg/kg body weight, FITC-F10 as a bolus of 12 mg/kg body weight, FITC-F5 as a bolus of 14 mg/kg body weight. The half-lives in FIG. 7B are 24.5+/−1.4 min for FITC-F10 and 19.9+/−0.9 min for S, and in FIG. 7C 30.0+/−0.6 min for FITC-F5 and 21.0+/−0.1 min for S.

FIG. 7D shows a comparison of the decrease in the relative concentrations for marked (FITC-F5, measurement values represented as rhombi) and non-marked F5 inulins (F5, measurement values represented as squares) over time.

FITC-F5 was administered as a bolus of 14 mg/kg body weight, and F5 as a bolus of 750 mg/kg body weight. The half-lives are 29.5+/−1.5 min for FITC-F5 and 21.9+/−0.6 min for F5. A significantly better marking efficiency can be inferred from the lower bolus administrations for FITC-F10 and FITC-F5 in comparison with FITC-S. The increased half-lives for FITC-F10 and FITC-F5 can be explained by the stronger lipophilic influence of the FITC group on the lipophilic properties of the overall molecule.

| List of reference symbols | |
|---|---|
| 110 | Kit for the transcutaneous measurement of an organ function |
| 112 | Indicator substance |
| 114 | Sensor system for the transcutaneous measurement of an organ function |
| 116 | Sensor plaster for the transcutaneous measurement of an organ function |
| 118 | Reader |
| 120 | Operating elements |
| 122 | Indicator element |
| 124 | Interface |
| 126 | Radio frequency interface |
| 128 | Wireless communication |
| 130 | Driving and evaluation electronic unit |
| 131 | Front side |
| 132 | Active area |
| 133 | Rear side |
| 134 | Carrier element |
| 136 | Sensor module |
| 138 | Adhesive surface |
| 140 | Optical unit |
| 142 | Light source |
| 144 | Excitation filter |
| 146 | Detector |
| 148 | Response filter |
| 150 | Electronic unit |
| 152 | Driving electronic unit |
| 154 | Communication unit |
| 156 | Interface |
| 158 | Electrical energy source |
| 159 | Energy generating device |
| 160 | Substrate material |
| 162 | Interrogation light |
| 164 | Transparent anode |
| 166 | Barrier layer |
| 168 | Hole transport material |
| 170 | Emitter material |
| 172 | Electro injection material |
| 174 | Cathode |
| 176 | Response light |
| 178 | Copper phthalocyanin |
| 180 | $C_{60}$ |
| 182 | Application of sensor plaster |
| 183 | Zero value measurement |
| 184 | Introduction of indicator substance |
| 186 | Detection |
| 188 | Storage |
| 190 | Repetition |
| 192 | Evaluation |
| 194 | Rat ear |
| 196 | Interstitial space |
| 198 | Blood vessels |

The invention claimed is:

1. A method for transcutaneously measuring a kidney function in a subject, comprising:
   (a) applying a sensor plaster (116) for the transcutaneous measurement of the kidney function, wherein the sensor plaster comprises:
      (i) at least one flexible carrier element (134) having at least one adhesive surface (138) which can be stuck onto a body surface,
      (ii) at least one radiation source, wherein the radiation source is designed to irradiate the body surface with at least one interrogation light (162), and wherein the radiation source is an integral constituent of the plaster, and
      (iii) at least one detector (146), wherein the detector (146) is designed to detect at least one response light (176) incident from the direction of the body surface;
   (b) administering at least one indicator substance by injection to the blood of the subject, wherein said indicator substance is a polyol covalently linked to a marker having optically measurable properties;
   (c) carrying out at least two temporally delimited measurements of the optically measurable properties of the indicator substance at different points in time and/or at least one continuous measurement over a time period in an interstitial fluid in a tissue; and
   (d) deducing a temporal profile of a concentration of an indicator substance from a temporal profile of the response light, thereby transcutaneously measuring the kidney function in the subject.

2. The method of claim 1, wherein the kidney function is determined for the purpose of (i) diagnosing an existing kidney dysfunction, (ii) determining the risk of further kidney of dysfunctions, (iii) monitoring in the case of diseases, therapeutic interventions or therapies which can cause kidney dysfunctions, or (iv) determining the individual dose for medicaments that are excreted via the kidney.

3. The method of claim 1, wherein the interrogation light and the response light in the sensor plaster are configured such that they are spectrally different.

4. The method of claim 1, wherein the at least one detector in the sensor plaster comprises at least one detector comprising at least one organic semiconducting material.

5. The method of claim 1, wherein the sensor plaster further comprises at least one filter element, or at least one imaging system, or at least one electrical energy storage device, or any combination thereof.

6. The method of claim 1, wherein the carrier element of the sensor plaster is configured such that it is at least substantially light-tight.

7. The method of claim 1, wherein the adhesive surface of the sensor plaster laterally encloses the detector, wherein, with the sensor plaster stuck onto the body surface, this prevents ambient light from being able to pass the detector.

8. The method of claim 1, wherein the sensor plaster is produced in a layer design and has at least two different layer planes.

9. The method of claim 1, wherein the polyol is selected from the group consisting of a polysaccharide, a cyclosaccharide, an insulin, a sinistrin, a fructosan, and a β-glycosidically linked di- or polysaccharide.

10. The method of claim 9, wherein the indicator substance is designed to be removed from the body substantially exclusively via the urinary tract.

11. The method of claim 1, wherein the kidney function is represented by glomerular filtration rate.

12. The method of claim 1, wherein said radiation source is a light-emitting diode.

13. The method of claim 1, wherein the sensor plaster (116) further comprises a driving electronic unit (152) designed to control a temporally resolved measurement of the optically measurable properties of the indicator.

14. The method of claim 1, wherein the temporal concentration profile of the indicator substance in the interstitial fluid of the subject serves as an indicator of the kidney function.

15. The method of claim 1, wherein the indicator substance is an indicator substance whose concentration is dependent substantially only on the kidney function.

\* \* \* \* \*

UNITED STATES PATENT AND TRADEMARK OFFICE
CERTIFICATE OF CORRECTION

PATENT NO. : 9,632,094 B2
APPLICATION NO. : 13/060260
DATED : April 25, 2017
INVENTOR(S) : Gretz et al.

Page 1 of 1

It is certified that error appears in the above-identified patent and that said Letters Patent is hereby corrected as shown below:

In the Claims

Column 36, Claim 9, Line 3, delete "an insulin" and insert therefor -- an inulin --.

Signed and Sealed this
Thirtieth Day of May, 2017

Michelle K. Lee
*Director of the United States Patent and Trademark Office*